United States Patent
Zhang et al.

(10) Patent No.: US 10,780,099 B2
(45) Date of Patent: Sep. 22, 2020

(54) INJECTABLE NEUROSTEROID FORMULATIONS CONTAINING NANOPARTICLES

(71) Applicant: MARINUS PHARMACEUTICALS, INC., Radnor, PA (US)

(72) Inventors: Mingbao Zhang, Millwood, NY (US); Raymond C. Glowaky, Killingworth, CT (US); David Czekai, Haverford, PA (US)

(73) Assignee: MARINUS PHARMACEUTICALS, INC., Radnor, PA (US)

( * ) Notice: Subject to any disclaimer, the term of this patent is extended or adjusted under 35 U.S.C. 154(b) by 0 days.

(21) Appl. No.: 15/294,135

(22) Filed: Oct. 14, 2016

(65) Prior Publication Data

US 2017/0258812 A1   Sep. 14, 2017

Related U.S. Application Data

(60) Provisional application No. 62/242,601, filed on Oct. 16, 2015.

(51) Int. Cl.

| A61K 31/573 | (2006.01) |
| A61K 9/00 | (2006.01) |
| A61K 9/10 | (2006.01) |
| A61K 9/19 | (2006.01) |
| A61K 47/36 | (2006.01) |
| A61K 47/32 | (2006.01) |
| A61K 47/24 | (2006.01) |
| A61K 31/57 | (2006.01) |
| A61K 9/14 | (2006.01) |
| A61K 9/16 | (2006.01) |
| A61K 45/06 | (2006.01) |

(52) U.S. Cl.
CPC .......... *A61K 31/573* (2013.01); *A61K 9/0019* (2013.01); *A61K 9/10* (2013.01); *A61K 9/146* (2013.01); *A61K 9/1611* (2013.01); *A61K 9/1617* (2013.01); *A61K 9/1623* (2013.01); *A61K 9/1641* (2013.01); *A61K 9/1652* (2013.01); *A61K 9/19* (2013.01); *A61K 31/57* (2013.01); *A61K 45/06* (2013.01); *A61K 47/24* (2013.01); *A61K 47/32* (2013.01); *A61K 47/36* (2013.01)

(58) Field of Classification Search
None
See application file for complete search history.

(56) References Cited

U.S. PATENT DOCUMENTS 4,783,484 A   11/1988   Violante et al.
4,826,689 A   5/1989   Violanto et al.

(Continued)

FOREIGN PATENT DOCUMENTS

CA   2541811        4/2005
CA   2892811 A1    6/2014

(Continued)

OTHER PUBLICATIONS

Chai et al., "Protective effect of polysaccharides on the stability of parenteral emulsions", 2013, Drug Development and Industrial Pharmacy, 39:5, pp. 646-656.*
Botella, M. G., et al., "Neuroactive Steroids. 1. Positive Allosteric Modulators of the (gamma-Aminobutyric Acid)a Receptor: Structure—Activity Relationships of Heterocyclic Substitution at C-21" Journal of Medicinal Chemistry, 2015, 58, pp. 3500-3511.
Hogenkamp et al.; "Synthesis and in Vitro Activity of 3Beta-Substituted-3Alpha-hydroxypregnan-20-ones:Allocteric Modulations of the GABA(A) Receptor"; J. Med. Chem. 40; pp. 61-72; (1997).

(Continued)

*Primary Examiner* — Robert A Wax
*Assistant Examiner* — Randeep Singh
(74) *Attorney, Agent, or Firm* — Hogan Lovells US LLP

(57) ABSTRACT

The disclosure provides an injectable neurosteroid nanoparticle formulation comprising nanoparticles having a D50 of less than 2000 nm the nanoparticles comprising a neurosteroid of Formula I,

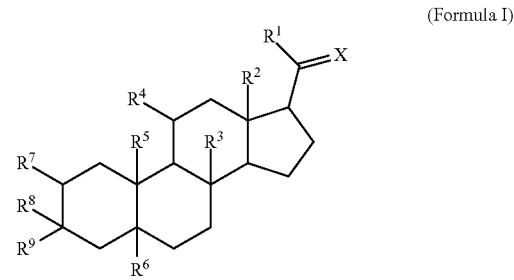

(Formula I)

where the variables $R^1$-$R^9$ and X are defined herein and at least one surface stabilizer. The surface stabilizer can be a polymeric surface stabilizer such as hydroxyethyl starch, dextran, or povidone. The injectable neurosteroid nanoparticle formulation can be an intravenous formulation. The disclosure also provides a lyophilized powder of the injectable neurosteroid nanoparticle formulation that can be reconstituted in an aqueous solution prior to administration. The disclosure provides injectable neurosteroid nanoparticle formulations and dry powders of such formulations that have been sterilized by ebeam irradiation. The disclosure provides a method of treating a patient having a seizure disorder, stroke, or traumatic brain injury, comprising administering an effective amount of the injectable neurosteroid nanoparticle formulation. The disclosure also provides combination methods in which the injectable neurosteroid nanoparticle formulation is a first active agent that is administered in combination with at least one additional active agent.

22 Claims, 7 Drawing Sheets

(56) References Cited

U.S. PATENT DOCUMENTS

| | | | |
|---|---|---|---|
| 4,997,454 A | 3/1991 | Violante et al. |
| 5,145,684 A | 9/1992 | Liversidge et al. |
| 5,298,262 A | 3/1994 | Na et al. |
| 5,346,702 A | 9/1994 | Na et al. |
| 5,352,459 A | 10/1994 | Hollister et al. |
| 5,399,363 A | 3/1995 | Liversidge et al. |
| 5,429,824 A | 7/1995 | June |
| 5,470,583 A | 11/1995 | Na et al. |
| 5,494,683 A | 2/1996 | Liversidge et al. |
| 5,508,040 A | 4/1996 | Chen |
| 5,510,118 A | 4/1996 | Bosch et al. |
| 5,518,187 A | 5/1996 | Bruno et al. |
| 5,534,270 A | 7/1996 | De Castro |
| 5,543,133 A | 8/1996 | Swanson et al. |
| 5,560,932 A | 10/1996 | Bagchi et al. |
| 5,573,783 A | 11/1996 | Desieno et al. |
| 5,662,883 A | 9/1997 | Bagchi et al. |
| 5,665,331 A | 9/1997 | Bagchi et al. |
| 5,718,388 A | 2/1998 | Czekai et al. |
| 5,741,522 A | 4/1998 | Violante et al. |
| 5,776,496 A | 7/1998 | Violante et al. |
| 5,862,999 A | 1/1999 | Czekai et al. |
| 6,039,979 A | 3/2000 | Gendrot et al. |
| 6,228,398 B1 | 5/2001 | Devane et al. |
| 6,267,989 B1 | 7/2001 | Liversidge et al. |
| 6,375,986 B1 | 4/2002 | Ryde et al. |
| 6,592,903 B2 | 7/2003 | Ryde et al. |
| 6,730,325 B2 | 5/2004 | Devane et al. |
| 6,793,936 B2 | 9/2004 | Devane et al. |
| 6,902,742 B2 | 6/2005 | Devane et al. |
| 6,908,626 B2 | 6/2005 | Cooper et al. |
| 6,969,529 B2 | 11/2005 | Bosch et al. |
| 7,078,057 B2 | 7/2006 | Kerkhof |
| 7,198,795 B2 | 4/2007 | Cooper et al. |
| 7,550,445 B2 | 6/2009 | Nerurkar et al. |
| 7,842,232 B2 | 11/2010 | Bosch et al. |
| 7,858,609 B2 | 12/2010 | Shaw et al. |
| 8,022,054 B2 | 9/2011 | Shaw et al. |
| 8,252,228 B1 * | 8/2012 | Freeman .................. A61L 2/081 |
| | | | 128/898 |
| 8,318,714 B2 | 11/2012 | Shaw et al. |
| 8,362,286 B2 | 1/2013 | Shaw et al. |
| 8,367,651 B2 | 2/2013 | Shaw et al. |
| 8,455,002 B2 | 6/2013 | Shaw et al. |
| 8,604,011 B2 | 12/2013 | Mellon |
| 8,618,087 B2 | 12/2013 | Shaw et al. |
| 8,658,692 B2 | 2/2014 | Kim et al. |
| 8,697,678 B2 | 4/2014 | Goodchild et al. |
| 8,975,245 B2 | 3/2015 | Goodchild et al. |
| 9,017,728 B2 | 4/2015 | Shaw et al. |
| 9,029,355 B2 | 5/2015 | Shaw et al. |
| 9,056,116 B2 | 6/2015 | Shaw et al. |
| 9,452,176 B2 | 9/2016 | Shaw et al. |
| 2002/0012675 A1 | 1/2002 | Jain et al. |
| 2003/0054042 A1 | 3/2003 | Liversidge et al. |
| 2003/0129242 A1 | 7/2003 | Bosch et al. |
| 2004/0067251 A1 | 4/2004 | Johnston et al. |
| 2004/0105778 A1 | 6/2004 | Lee et al. |
| 2004/0105889 A1 | 6/2004 | Ryde et al. |
| 2004/0214746 A1 | 10/2004 | Bosch et al. |
| 2004/0258757 A1 | 12/2004 | Bosch et al. |
| 2005/0031691 A1 | 2/2005 | McGurk et al. |
| 2005/0118268 A1 | 6/2005 | Percel et al. |
| 2005/0196416 A1* | 9/2005 | Kipp ..................... A61K 9/1075 |
| | | | 424/400 |
| 2006/0216353 A1 | 9/2006 | Liversidge et al. |
| 2007/0141161 A1 | 6/2007 | Shaw et al. |
| 2007/0148252 A1 | 6/2007 | Shaw et al. |
| 2009/0004262 A1 | 1/2009 | Shaw et al. |
| 2011/0236487 A1 | 9/2011 | Shaw et al. |
| 2011/0306579 A1* | 12/2011 | Stein ..................... A61K 31/56 |
| | | | 514/167 |
| 2012/0052098 A1 | 3/2012 | Shaw et al. |
| 2014/0057885 A1 | 2/2014 | Reddy et al. |
| 2014/0066417 A1 | 3/2014 | Goodchild et al. |
| 2014/0235600 A1 | 8/2014 | Covey et al. |
| 2014/0249120 A1 | 9/2014 | Covey et al. |
| 2015/0018327 A1 | 1/2015 | Reddy |
| 2015/0158903 A1 | 6/2015 | Upasani et al. |
| 2015/0175651 A1 | 6/2015 | Salituro et al. |
| 2015/0291654 A1 | 10/2015 | Upasani et al. |
| 2015/0315230 A1 | 11/2015 | Covey et al. |
| 2015/0335659 A1 | 11/2015 | Jones et al. |
| 2016/0228454 A1 | 8/2016 | Zhang et al. |
| 2017/0202855 A1 | 7/2017 | Shaw et al. |
| 2018/0071315 A1 | 3/2018 | Cashman et al. |

FOREIGN PATENT DOCUMENTS

| | | |
|---|---|---|
| EP | 0169618 A2 | 1/1986 |
| EP | 0498824 B1 | 8/1992 |
| EP | 0499299 A2 | 8/1992 |
| EP | 0580690 A1 | 2/1994 |
| WO | 9526715 A2 | 10/1995 |
| WO | 9857648 A1 | 12/1998 |
| WO | 0145677 A1 | 6/2001 |
| WO | 2007062266 A2 | 5/2007 |
| WO | 2008066899 A2 | 6/2008 |
| WO | 2011088503 A1 | 7/2011 |
| WO | 2013063279 A1 | 5/2013 |
| WO | 2013112605 A2 | 8/2013 |
| WO | 2014085668 A1 | 6/2014 |
| WO | 2014127201 A1 | 8/2014 |
| WO | 2014160441 A1 | 10/2014 |
| WO | 2014160480 A1 | 10/2014 |
| WO | 2014169831 A1 | 10/2014 |
| WO | 2014169832 A1 | 10/2014 |
| WO | 2014169833 A1 | 10/2014 |
| WO | 2014169836 A1 | 10/2014 |
| WO | 2015010054 A2 | 1/2015 |
| WO | 2015027227 A1 | 2/2015 |
| WO | 2015081170 A1 | 6/2015 |
| WO | 2015180679 A1 | 12/2015 |
| WO | 2016040322 A1 | 3/2016 |
| WO | 2016127170 A1 | 8/2016 |

OTHER PUBLICATIONS

International Search Report for International Application No. PCT/US2016/057120, dated Jan. 31, 2017, 6 Pages.

International Search Report of the International Searching Authority for International Application No. PCT/US2016/016977; Date of Filing: Feb. 8, 2016; dated Apr. 26, 2016; 6 pages.

Liptakova et al.; "Effect of Ganaxolone on Flurothyl Seizures in Developing Rats"; Epilepsia, vol. 47, No. 7; Jan. 2000; pp. 788-793.

Monaghan et al., "Initial Human Experience with Ganaxolone, a Neuroactive Steroid with Antiepileptic Activity" Epilepsia, 1997, vol. 38, Issue 9, pp. 1026-1031.

Moyne, P., et al., "Sterilization of injectable drugs solutions by irradiation" Radiation Physics and Chemistry, vol. 63 (2002) pp. 703-704.

Mula; "Emerging drugs for focal epilepsy"; Expert Opinion, vol. 18, No. 1; Mar. 2013; pp. 87-95.

Nohria et al.; "Ganaxolone"; The Journal of the American Society for Experimental NeuroTherapeutics; 4; pp. 102-105; (2007).

Pieribone, A. V., et al., "Clinical Evaluation of Ganaxolone in Pediatric and Adolescent Patients with Refractory Epilepsy" Epilepsia, vol. 48, No. 10, 2007, 5 pages.

Pramanick et al.; "Excipient Selection in Parenteral Formulation Development"; Pharma Times, vol. 45, No. 3; Mar. 2013; pp. 65-77.

Rogawski et al.; "Neuroactive Steroids for the Treatment of Status Epilepticus"; Epilepsia, vol. 54, No. 6; 2013; pp. 93-98.

Rosetti et al.; "Management of Refractory Status Epilepticus in Adults: Still More Questions Than Answers"; Lancet Nuerol., vol. 10; Oct. 2011; pp. 922-930.

Shorvon et al.; "The Treatment of Super-Refractory Status Epilepticus: A Critical Review of Available Therapies and a Clinical Treatment Protocol"; Brain, vol. 134; 2011; pp. 2802-2818.

Wong, J., et al. "Suspensions for intravenous (IV) injection: A review of development, preclinical and clinical aspects" Advanced Drug Delivery Reviews, vol. 60 (2008) pp. 939-954.

(56) References Cited

OTHER PUBLICATIONS

Written Opinion of the International Searching Authority for International Application No. PCT/US2016/016977; Date of Filing: Feb. 8, 2016; dated Apr. 26, 2016; 8 pages.
Written Opinion of the International Searching Authority for International Application No. PCT/US2016/057120, dated Jan. 31, 2017, 8 pages.
Marques, Margareth R.C., et al, "Simulated Biological Fluids with Possible Application in Dissolution Testing," Dissolution Technologies; Aug. 2011, pp. 15-28.
International Search Report and Written Opinion for Singapore Application No. 11201802309U; Application Filing Date—Oct. 14, 2016; dated Jun. 4, 2019, 11 pages.
"VFEND Full Prescribing Information," Roerig, Division of Pfizer, Inc., Lab-1348-1.0, revised Jan. 2019, 37 pages.
"Captisol," Accessed from www.captisol.com website maintained by Ligand on Sep. 26, 2019, five pages.
Horioka et al., "Injection Agent—Basics, Preparations, and Applications," Nanzando Co. Ltd. (1995), pp. 20-25.

\* cited by examiner

INJECTABLE NEUROSTEROID FORMULATIONS CONTAINING NANOPARTICLES

CROSS REFERENCE TO RELATED APPLICATION

This application claims priority from U.S. Provisional Application Ser. No. 62/242,601, filed Oct. 16, 2015, which is hereby incorporated by reference in its entirety.

BACKGROUND

Pregnane neurosteroids are a class of compounds useful as anesthetics, sedatives, hypnotics, anxiolytics, and anticonvulsants. These compounds are marked by very low aqueous solubility, which limits their formulation options. Injectable formulations of pregnane neurosteroids are particularly desirable as these compounds are used for clinical indications for which oral administration is precluded, such as anesthesia and particularly for the treatment of active seizures.

Status epilepticus (SE) is a serious seizure disorder in which the epileptic patient experiences a seizure lasting more than five minutes, or more than one seizure in a five minute period without recovering between seizures. In certain instances convulsive seizures may last days or even weeks. Status epilepticus is treated in the emergency room with conventional anticonvulsants. GABAA receptor modulators such as benzodiazepines (BZs) are a first line treatment. Patients who fail to respond to BZs alone are usually treated with anesthetics or barbiturates in combination with BZs. About 23-43% of status epilepticus patients who are treated with a benzodiazepine and at least one additional antiepileptic drug fail to respond to treatment and are considered refractory (Rossetti, A. O. and Lowenstein, D. H., *Lancet Neurol.* (2011) 10(10): 922-930.) There are currently no good treatment options for these patients. The mortality rate for refractory status epilepticus (RSE) patients is high and most RSE patients do not return to their pre-RSE clinical condition. About 15% of patients admitted to hospital with SE are in a subgroup of RSE patients said to be super-refractory SE (SRSE), in which the patients have continued or recurrent seizures 24 hours or more after the onset of anesthetic therapy. SRSE is associated with high rates of mortality and morbidity. (Shorvon, S., and Ferlisi, M., *Brain*, (2011) 134(10): 2802-2818.)

Another serious seizure disorder is PCDH19 female pediatric epilepsy, which affects approximately 15,000-30,000 females in the United States. This genetic disorder is associated with seizures beginning in the early years of life, mostly focal clustered seizures that can last for weeks. The mutation of the PCDH19 gene has been associated with low levels of allopregnanolone. Currently there are no approved therapies for PCDH19 female pediatric epilepsy.

Thus, there exists the need for additional treatments for seizure disorders such as status epilepticus, refractory status epilepticus, super refractory status epilepticus, and PCDH19 female pediatric epilepsy. This disclosure fulfills this need by providing injectable pregnane neurosteroid formulations and provides additional advantages that are described herein.

SUMMARY

The disclosure provides an injectable nanoparticle pregnane neurosteroid formulation comprising nanoparticles having a D50 (volume weighted median diameter) of less than 2000 nm (nanometers) and the nanoparticles comprising a pregnane neurosteroid, at least one surface stabilizer, for example a polymer surface stabilizer such as hydroxyethyl starch, dextran, or povidone, and in some embodiment an additional surface stabilizer, such as a surfactant. An embodiment of the formulation comprises the nanoparticles in an aqueous suspension. The disclosure also provides a lyophilized powder of the pregnane neurosteroid nanoparticle formulation that may be reconstituted in water for injection.

The disclosure provides a neurosteroid formulation comprising nanoparticles having a D50 of less than 2000 nm, the nanoparticles comprising~
a) a neurosteroid of Formula I:

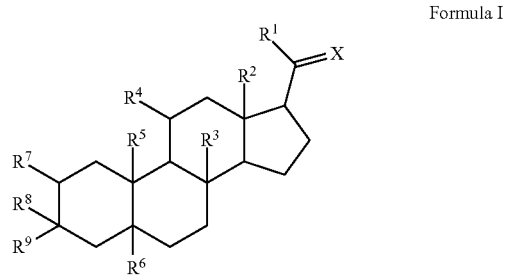

Formula I or a pharmaceutically acceptable salt thereof, wherein:
X is O, S, or $NR^{10}$;
$R^1$ is hydrogen, hydroxyl, optionally substituted alkyl, optionally substituted heteroalkyl, optionally substituted aryl, or optionally substituted arylalkyl;
$R^4$ is hydrogen, hydroxyl, oxo, optionally substituted alkyl, or optionally substituted hetero alkyl,
$R^2$, $R^3$, $R^5$, $R^6$, and $R^7$ are each independently hydrogen, hydroxyl, halogen, optionally substituted alkyl, or optionally substituted heteroalkyl;
$R^8$ is hydrogen or alkyl and $R^9$ is hydroxyl; or
$R^8$ and $R^9$ are taken together to form an oxo group;
$R^{10}$ is hydrogen, hydroxyl, optionally substituted alkyl, optionally substituted heteroalkyl, optionally substituted aryl, or optionally substituted arylalkyl where
each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;
each heteroalkyl group is an alkyl group in which one or more methyl group is replaced by an independently chosen —O—, —S—, —N($R^{10}$)—, —S(═O)— or —S(═O)$_2$—, where $R^{10}$ is hydrogen, alkyl, or alkyl in which one or more methylene group is replaced by —O—, —S—, —NH, or —N-alkyl; and
b) at least one surface stabilizer.

The disclosure also includes embodiments of the above injectable neurosteroid nanoparticle formulation in which the nanoparticles have a D50 of less than 500 which contain a surfactant as an additional surface stabilizer. The disclosure also includes neurosteroid nanoparticles having a D50 of less than 500 nm, the nanoparticles comprising
a) a compound or salt of Formula I;
b) a polymeric surface stabilizer; and
c) at least one additional surface stabilizer, wherein the additional surface stabilizer is a surfactant.

In certain embodiments the neurosteroid is ganaxolone (GNX) or allopregnanolone (ALLO). In certain embodiments the neurosteroid is ganaxolone.

The disclosure also provides a method of treating a patient having a seizure disorder, stroke, or traumatic brain injury, comprising administering an effective amount of the injectable neurosteroid nanoparticle formulation comprising a neurosteroid of Formula I (e.g. ganaxolone or allopregnanolone), either hydroxyethyl starch, dextran, or povidone, and a surfactant, in the form of nanoparticles; and water.

The disclosure includes methods of treatment in which the neurosteroid is the only active agent and methods in which the neurosteroid, of the neurosteroid nanoparticle formulation, is a first active agent and is administered in combination with an additional active agent.

The disclosure includes methods of treatment which include administration schedules for the neurosteroid nanoparticle formulation, in which the neurosteroid is the only active agent or in which the method includes treatment with at least one additional active agent.

DETAILED DESCRIPTION

Definitions

Figure 1:
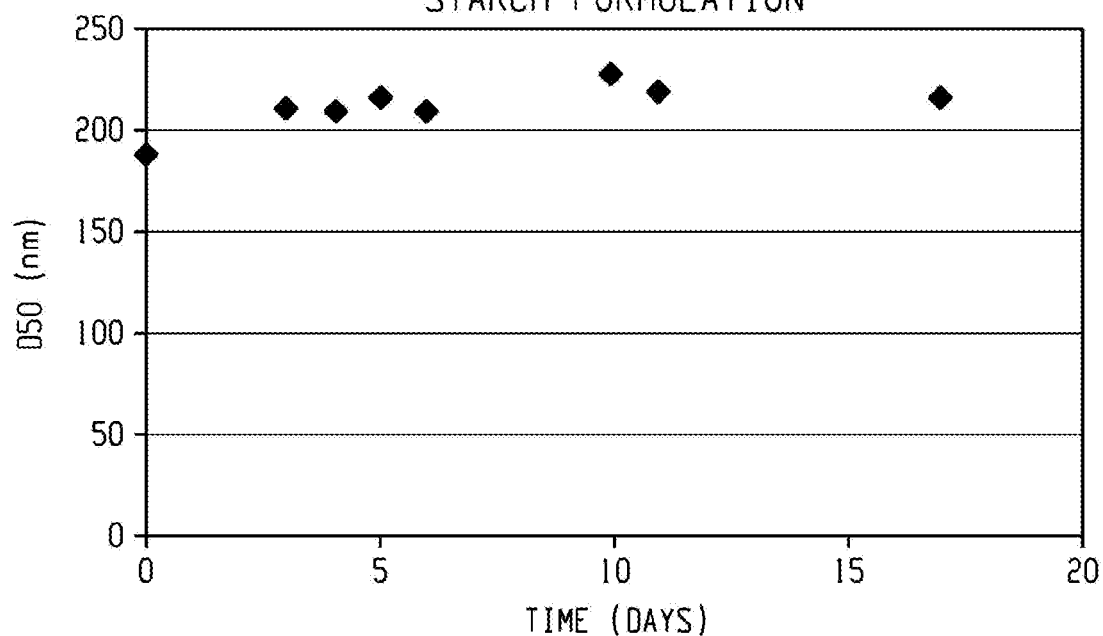
FIG. 1. D50 values of a ganaxolone nanosuspension stabilized by hydroxyethyl starch and sodium deoxycholate monitored over a 17-day period. The nanosuspension contained ganaxolone (20%), hydroxyethyl starch (6%), sodium deoxycholate (1.2%), and simethicone (0.06%). The particle size was substantially unchanged over the period monitored.

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed. No language in the specification should be construed as indicating any non-claimed element as essential to the practice of the invention.

The terms "a" and "an" do not denote a limitation of quantity, but rather denote the presence of at least one of the referenced item.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. Thus compositions slightly outside the cited ranges are also encompassed by the scope of the present claims.

An "active agent" is any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers in pure form and mixtures thereof are encompassed. In addition, compounds with carbon-carbon double bonds may occur in Z- and E-forms, with all isomeric forms of the compounds being included in the present invention. In these situations, the single enantiomers, i.e. optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The terms "comprising," "including," and "containing" are non-limiting. Other non-recited elements may be present in embodiments claimed by these transitional phrases. Where "comprising," "containing," or "including" are used as transitional phrases other elements may be included and still form an embodiment within the scope of the claim. The open-ended transitional phrase "comprising" encompasses the intermediate transitional phrase "consisting essentially of" and the close-ended phrase "consisting of."

"Alkyl" is a branched or straight chain saturated aliphatic hydrocarbon group, having the specified number of carbon atoms, generally from 1 to about 8 carbon atoms. The term $C_1$-$C_6$-alkyl as used herein indicates an alkyl group having from 1, 2, 3, 4, 5, or 6 carbon atoms. Other embodiments include alkyl groups having from 1 to 6 carbon atoms, 1 to 4 carbon atoms or 1 or 2 carbon atoms, e.g. $C_1$-$C_8$-alkyl, $C_1$-$C_4$-alkyl, and $C_1$-$C_2$-alkyl. Examples of alkyl include, but are not limited to, methyl, ethyl, n-propyl, isopropyl, n-butyl, 3-methylbutyl, t-butyl, n-pentyl, and sec-pentyl.

"Aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Aryl groups include, for example, phenyl, naphthyl, including 1-naphthyl, 2-naphthyl, and bi-phenyl. An "arylalkyl" substituent group is an aryl group as defined herein, attached to the group it substitutes via an alkylene linker. The alkylene is an alkyl group as described herein except that it is bivalent.

A "bolus dose" is a relatively large dose of medication administered in a short period, for example within 1 to 30 minutes.

$C_{max}$ is the measured concentration of an active concentration in the plasma at the point of maximum concentration.

"Cycloalkyl" is a saturated hydrocarbon ring group, having the specified number of carbon atoms. Monocyclic cycloalkyl groups typically have from 3 to about 8 carbon ring atoms or from 3 to 6 (3, 4, 5, or 6) carbon ring atoms. Cycloalkyl substituents may be pendant from a substituted nitrogen, oxygen, or carbon atom, or a substituted carbon atom that may have two substituents may have a cycloalkyl group, which is attached as a spiro group. Examples of cycloalkyl groups include cyclopropyl, cyclobutyl, cyclopentyl, and cyclohexyl.

A "heteroalkyl" group is an alkyl group as described with at least one carbon replaced by a heteroatom, e.g. N, O, or S.

"Infusion" administration is a non-oral administration, typically intravenous though other non-oral routes such as epidural administration are included in some embodiments. Infusion administration occurs over a longer period than a bolus administration, for example over a period of at least 15 minutes, at least 30 minutes, at least 1 hour, at least 2 hours, at least 3 hours, or at least 4 hours.

A "patient" is a human or non-human animal in need of medical treatment. Medical treatment includes treatment of an existing condition, such as a disorder or injury. In certain embodiments treatment also includes prophylactic or preventative treatment, or diagnostic treatment.

"Pharmaceutical compositions" are compositions comprising at least one active agent, such as a compound or salt, solvate, or hydrate of Formula (I), and at least one other substance, such as a carrier. Pharmaceutical compositions optionally contain one or more additional active agents. When specified, pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as a seizure disorder.

"Povidone" also known as polyvidone and polyvinylpyrrolidone (PVP) is a water soluble polymer made from the monomer, N-vinylpyrrolidone. Plasdone C-12 and C-17 are pharmaceutical grade homopolymers of N-vinylpyrrolidone. Plasdone C-12 has a K value of 10-2-13.8 and nominal molecular weight of 4000 d. Plasdone C-17 has a K-value of 15.5-17.5 and nominal molecular weight of 10,000 d.

The term "substituted" as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, e.g., halogen; cyano; —OH; oxo; —NH$_2$; nitro; azido; alkanoyl (such as a C$_2$-C$_6$ alkanoyl group); C(O)NH$_2$; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; mono- or dialkylamino groups including groups having alkyl groups from 1 to about 6 carbon atoms; mono- or dialkylaminocarbonyl groups (i.e. alkylN- HCO— or (alkyl1)(alkyl2)NCO—) having alkyl groups from about 1 to about 6 carbon atoms; aryl having 6 or more carbons.

"Sterilize" means to inactivate substantially all biological contaminates in a sample, formulation, or product. A 1-million fold reduction in the bioburden is also considered "sterilized" for most pharmaceutical applications.

A "therapeutically effective amount" or "effective amount" is that amount of a pharmaceutical agent to achieve a pharmacological effect. The term "therapeutically effective amount" includes, for example, a prophylactically effective amount. An "effective amount" of neurosteroid is an amount needed to achieve a desired pharmacologic effect or therapeutic improvement without undue adverse side effects. The effective amount of neurosteroid will be selected by those skilled in the art depending on the particular patient and the disease. It is understood that "an effective amount" or "a therapeutically effective amount" can vary from subject to subject, due to variation in metabolism of neurosteroid, age, weight, general condition of the subject, the condition being treated, the severity of the condition being treated, and the judgment of the prescribing physician.

"Treat" or "treatment" refers to any treatment of a disorder or disease, such as inhibiting the disorder or disease, e.g., arresting the development of the disorder or disease, relieving the disorder or disease, causing regression of the disorder or disease, relieving a condition caused by the disease or disorder, or reducing the symptoms of the disease or disorder.

Chemical Description

The disclosure includes injectable nanoparticle neurosteroid formulations. The neurosteroid may be a compound of Formula I. Formula I includes allopregnanolone, ganaxolone, alphaxalone, alphadolone, hydroxydione, minaxolone, pregnanolone, acebrochol, or tetrahydrocorticosterone.

Ganaxolone (CAS Reg. No. 38398-32-2, 3α-hydroxy, 3β-methyl-5α-pregnan-20-one) is a synthetic steroid with anti-convulsant activity useful in treating epilepsy and other central nervous system disorders.

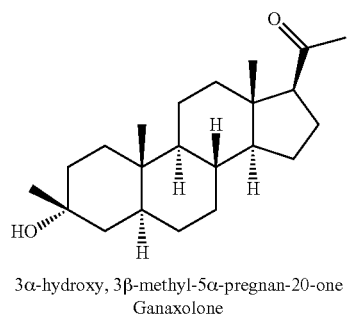

3α-hydroxy, 3β-methyl-5α-pregnan-20-one
Ganaxolone

Ganaxolone has a relatively long half-life—approximately 20 hours in human plasma following oral administration (Nohria, V. and Giller, E., *Neurotherapeutics*, (2007) 4(1): 102-105). Furthermore, ganaxolone has a short $T_{max}$, which means that therapeutic blood levels are reached quickly. Thus initial bolus doses (loading doses) may not be required, which represents an advantage over other treatments. Ganaxolone is useful for treating seizures in adult and pediatric epileptic patients.

Allopregnanolone (CAS Reg. No. 516-54-1, 3α,5α-tetrahydroprogesterone) is an endogenous progesterone derivative with anti-convulsant activity.

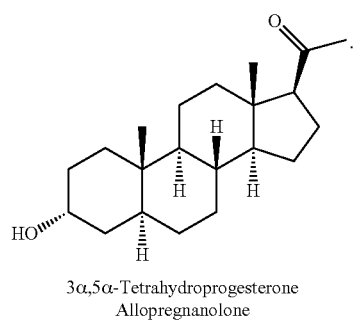

3α,5α-Tetrahydroprogesterone
Allopregnanolone

Allopregnanolone has a relatively short half-life, about 45 minutes in human plasma. In addition to its efficacy in treating seizures, allopregnanolone is being evaluated for use in treating neurodegenerative diseases including Alzheimer's disease, Parkinson's disease, Huntington's disease, and amyotrophic lateral sclerosis and for treating lysosomal storage disorders characterized by abnormalities in cholesterol synthesis, such as Niemann Pick A, B, and C, Gaucher disease, and Tay Sachs disease. (See U.S. Pat. No. 8,604,011, which is hereby incorporated by reference for its teachings regarding the use of allopregnanolone for treating neurological disorders.)

Alphaxalone, also known as alfaxalone, (CAS Reg. No. 23930-19-0, 3α-hydroxy-5α-pregnan-11,20-dione) is a neurosteroid with an anesthetic activity. It is used as a general anaesthetic in veterinary practice. Anaesthetics are frequently administered in combination with anti-convulsants for the treatment of refractory seizures. An injectable nanoparticle neurosteroid dosage form containing alphaxalone alone or in combination with either ganaxolone or allopregnanolone is within the scope of this disclosure.

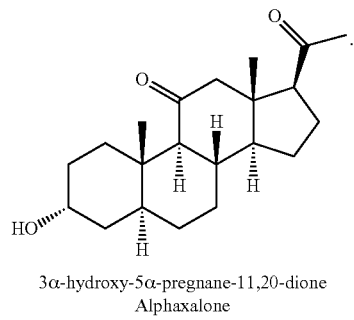

3α-hydroxy-5α-pregnane-11,20-dione
Alphaxalone

Alphadolone, also known as alfadolone, (CAS Reg. No. 14107-37-0, 3α,21-dihydroxy-5α-pregnan-11,20-dione) is a neurosteroid with anaesthetic properties. Its salt, alfadolone acetate is used as a veterinary anaesthetic in combination with alphaxalone.

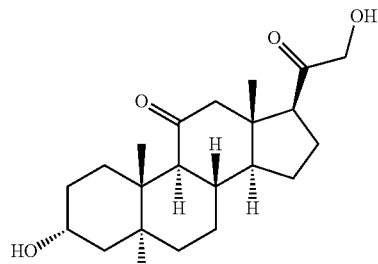

3α-21-dihydroxy-5α-pregnane-11,20-dione
Alphadolone

Additional neurosteroids that may be used in the injectable nanoparticle neurosteroid formulation of this disclosure include formulations include hydroxydione (CAS Reg. No. 303-01-5, (5β)-21-hydroxypregnane-3,20-dione), minaxolone (CAS Reg. No. 62571-87-3, 2β,3,3α,5α,11α)-11-(dimethylamino)-2-ethoxy-3-hydroxypregnan-20-one), pregnanolone (CAS Reg. No. 128-20-1, (3α,5β)d-hydroxypreganan-20-one), renanolone (CAS Reg. No. 565-99-1, 3α-hydroxy-5β-pregnan-11,20-dione), or tetrahydrocorticosterone (CAS Reg. No. 68-42-8, 3α,5α-pregnan-20-di-one).

Neurosteroid Nanoparticles

This disclosure is directed to injectable nanoparticle formulations, including formulations suitable for intravenous administration. The neurosteroid nanoparticles contain a neurosteroid of Formula I, a surface stabilizer, and a surfactant. In certain embodiments the neurosteroid, may be ganaxolone or allopregnanolone.

This disclosure is also directed to neurosteroid nanoparticles a neurosteroid of Formula I, a surface stabilizer, and a surfactant.

The disclosure provides injectable neurosteroid nanoparticle formulations, including formulations containing nanoparticles comprising a neurosteroid of Formula I, at least one surface stabilizer, such as hydroxyethyl starch, dextran, or povidone and a surfactant. In certain embodiments the nanoparticles comprise ganaxolone or allopregnanolone, hydroxyethyl starch, and a surfactant. Injectable neurosteroid nanoparticle formulations disclosed herein include formulations suitable for intramuscular, intravenous, intraarterial, intraspinal, subcutaneous and intrathecal injection. Injectable formulations include parenteral formulations suitable for intravenous infusion.

Many neurosteroids are very poorly soluble in water and thus difficult to formulate as aqueous injectable dosage forms. For example, ganaxolone is very poorly soluble in water (<0.001 mg/mL). The inventors have found that neurosteroids may be formulated as an aqueous injectable suspension by preparing the neurosteroid as a nanoparticle, the nanoparticle particle containing a polymeric surface stabilizer, such as either hydroxyethyl starch, dextran, or povidone, and an additional surface stabilizer, and the additional surface stabilizer is a surfactant.

The injectable neurosteroid nanoparticle formulation includes a surface stabilizer. In certain embodiment the surface stabilizer is a blood replacer, such as a blood volume expander. In certain embodiments the surface stabilizer is either hydroxyethyl starch, dextran, or povidone. Hydroxyethyl starch is used as a blood volume expander in patients suffering from severe blood loss. Grades of hydroxyethyl starch suitable for use in the neurosteroid nanoparticles include 130/0.4 (CAS Reg. No. 9005-27-0). In certain embodiments the surface stabilizer is dextran. Dextran is a single chain branched glucan having chains of varying lengths. Like hydroxyethyl starch, dextran is also used as a blood volume expander. Dextrans are classified according to MW. Dextrans having molecular weights from 40 kD to 75 kD have been used as blood volume expanders. Suitable dextrans for intravenous use include Dextran 40, Dextran 60, Dextran 70, and Dextran 75. In certain embodiments the surface stabilizer is a dextran having a molecular weight from about 40 kD to about 75 kD. In certain embodiments the surface stabilizer is Dextran 70. Povidone, also known as polyvinylpyrrolidone, is another approved plasma expander. Povidone includes PLASDONE C-12 and C-17 from Ashland, Inc.

Other excipients useful as surface stabilizers for the injectable neurosteroid nanoparticle formulation include human serum albumin, hydrolyzed gelatin, polyoxyethylene castor oil, and polyoxyethylene hydrogentated castor oil. The injectable neurosteroid nanoparticle injectable formulation includes a surfactant.

Surfactants include compounds such as lecithin (phosphatides), sorbitan trioleate and other sorbitan esters, polyoxyethylene sorbitan fatty acid esters (e.g., the commercially available PATENS such as polyoxyethylene sorbitan monolaurate (TWEEN 20) and polyoxyethylene sorbitan monooleate (TWEEN 80) (ICI Speciality Chemicals)); poloxamers (e.g., poloxamer 188 PLURONIC F68 and poloxamer 338 (PLURONIC F108), which are block copolymers of ethylene oxide and propylene oxide), lecithin, sodium cholesterol sulfate or other cholesterol salts, and bile salts, such as sodium deoxycholate. Additional bile salts that may be used as surfactants include sodium cholate, sodium glycholate, salts of deoxycholic acid, salts of glycholic acid, salts of chenodeoxycholic acid, and salts of lithocholic acid.

The disclosure includes neurosteroid nanoparticles having a volume weighted median diameter (D50) of from about 50 nm to about 2000 nm, about 50 nm about 500 nm, about 10 nm to about 350 nm, or having a D50 of from about 50 nm to about 300 nm, or having a D50 of from about 100 nm to about 250 nm, or having a D50 of about 150 nm to about 220 nm, or having a D50 of less than 2000 nm, less than 500 nm, of less than 350 nm, less than 300 nm, less than 250 nm, or less than 200 nm. In one aspect the neurosteroid nanoparticles have at least one of the following properties: (a) greater than 90% of the neurosteroid by weight is in the form of submicron particle having an effective size of about 50 nm to about 250 nm; (b) at least about 20% of the neurosteroid by weight is in the form of an amorphous powder; (c) at least about 50% of the neurosteroid by weight is in the form of a crystalline powder of a single polymorph; (d) at least about 50% of the neurosteroid is in the form of a semi-crystalline powder; (e) the neurosteroid is in the form of particles wherein at least about 50%, or at least 60%, or at least 70%, or at least 80%, or at least 90% of the particles by weight have an effective size less than 300 nm; (f) the neurosteroid is in the form of particles wherein at least about 50% of the particles by weight have an effective size less than 250 nm; (g) the neurosteroid is in the form of particles having a D50 of about 50 nm to about 200 nm, wherein the particle size distribution is described by a three-slice model in which a certain percentage has an effective particle size by weight between about 10 nm and about 100 nm, a certain percentage has an effective particle size by weight between about 100 nm and about 200 nm, and a certain percentage has an effective particle size by weight above 200 nm, and further wherein the three-slice model is identified as x %/y %/z %, respectively (e.g., 40%/30%/30%); (p) the neurosteroid has a three-slice distribution selected from the group 40%/30%/30%, 50%/30%/20%, 60%/30%/10%, 40%/40%/20%, 50%/40%/10%, 70%/20%/10%, 50%/45%/5%, 70%/25%/5%, 60%/35%/5%, 80%/15%/5%, 70%/30%/0%, 60%/40%/0%, 90%/10%/0%, and 100%/0%/0%; (h) the neurosteroid is in the form of particles, wherein standard deviation of the particle size distribution divided by the volume-weighted mean diameter is less than about 30%, less than about 25%, less than about 20%, less than about 15%, or less than about 10%. In alternative embodiments, the neurosteroid in the composition has at least two of the aforementioned properties; at least about three of the aforementioned properties; at least about four of the aforementioned properties; or at least five of the aforementioned properties.

The neurosteroid nanoparticles may be prepared by grinding. Grinding can take place in any suitable grinding mill. Suitable mills include an air jet mill, a roller mill, a ball mill, an attritor mill, a vibratory mill, a planetary mill, a sand mill and a bead mill. A high energy media mill is preferred when small particles are desired. The mill can contain a rotating shaft.

The preferred proportions of the grinding media, neurosteroid, the optional liquid dispersion medium, and dispersing, wetting or other particle stabilizing agents present in the grinding vessel can vary within wide limits and depends, for example, the size and density of the grinding media, the type of mill selected, the time of milling, etc. The process can be carried out in a continuous, batch or semi-batch mode. In high energy media mills, it can be desirable to fill 80-95% of the volume of the grinding chamber with grinding media. On the other hand, in roller mills, it frequently is desirable to leave the grinding vessel up to half filled with air, the remaining volume comprising the grinding media and the liquid dispersion media, if present. This permits a cascading effect within the vessel on the rollers which permits efficient grinding. However, when foaming is a problem during wet grinding, the vessel can be completely filled with the liquid dispersion medium or an anti-foaming agent may be added to the liquid dispersion.

The attrition time can vary widely and depends primarily upon the drug, mechanical means and residence conditions selected, the initial and desired final particle size and so forth.

After attrition is completed, the grinding media is separated from the milled neurosteroid particulate product (in either a dry or liquid dispersion form) using conventional separation techniques, such as by filtration, sieving through a mesh screen, and the like.

In one aspect, the grinding media comprises beads having a size ranging from 0.05-4 mm, preferably 0.1-0.4 mm. For example, high energy milling of neurosteroid with yttrium stabilized zirconium oxide 0.4 mm beads for a milling residence time of 25 minutes to 1.5 hours in recirculation mode at 2500 RPM. In another example, high energy milling of neurosteroid with plastic heads (e.g. Purolite® Puromill 300) for a milling time of 400 minutes in recirculation mode at 4200 RPM. In another example, high energy milling of neurosteroid with 0.1 mm zirconium oxide balls for a milling residence time of 2 hours in batch mode. Additionally, the milling temperature should not exceed 50° C. as the viscosity of the suspension may change dramatically. The milling concentration is from about 1% to about 40% neurosteroid by weight. In one embodiment, the concentration is 25% neurosteroid by weight. In one embodiment, the milling media contains at least one agent to adjust viscosity so that the desired particles are suspended evenly, and a wetting and/or dispersing agent to coat the initial neurosteroid suspension so a uniform feed rate may be applied in continuous milling mode. In another embodiment, batch milling mode is utilized with a milling media containing at least one agent to adjust viscosity and/or provide a wetting effect so that the neurosteroid is well dispersed amongst the grinding media.

Injectable Neurosteroid Nanoparticle Formulations

The disclosure provides injectable neurosteroid nanoparticle formulations containing the neurosteroid at a concentration of about 0.25 mg/mL, about 0.5 mg/mL, about 1.0 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/L, about 8.0 mg/mL, about 8.5 mg/mL, about 9.0 mg/mL, about 10 mg/mL, about 11 mg/mL, about 12 mg/mL, about 13 mg/mL, or about 15 mg/mL. All ranges including any two of the foregoing concentrations of neurosteroid as endpoints are also included in the disclosure. For example, the disclosure includes neurosteroid nanoparticle formulations containing from about 0.5 mg/mL, to about 15 mg/mL, about 1.0 mg/mL to about 10 mg/mL about 2.0 mg/mL to about 8.0 mg/mL, or about 4.0 mg/mL to about 8.0 mg/mL neurosteroid.

The nanoparticles will include neurosteroid and a surface stabilizer, such as either hydroxyethyl starch, povidone, or dextran, in a weight to weight ratio of neurosteroid to surface stabilizer is about 10:1 to 0.5:1, or about 5:1 to about 0.5:1, or about 4:1 to about 1:1, or about 3.5:1 to about 3:1, or about 3.3:1.

The disclosure includes embodiments in which the injectable neurosteroid nanoparticle formulation additionally comprises a buffer. In certain embodiments the buffer is a phosphate buffer. In certain embodiments the buffer is phosphate buffered saline.

The injectable neurosteroid nanoparticle formulations may also include an acid or base buffer to adjust pH to desired levels. In some embodiments the desired pH is 2.5-11.0, 3.5-9.0, or 5.0-8.0, or 6.0-8.0, or 7.0-7.6, or about 7.4, Examples of acid buffers useful in the injectable neurosteroid nanoparticle formulation include oxalic acid, maleic acid, fumaric acid, lactic acid, malic acid, tartaric acid, citric acid, benzoic acid, acetic acid, methanesulfonic acid, histidine, succinic acid, toluenesulfonic acid, benzenesulfonic acid, ethanesulfonic acid and the like. Acid salts of the above acids may be employed as well. Examples of base buffers useful in the formulation include carbonic acid and bicarbonate systems such as sodium carbonate and sodium bicarbonate, and phosphate buffer systems, such as sodium monohydrogen phosphate and sodium dihydrogen phosphate. The concentration of each component of a phosphate buffer system will be from about 10 mM to about 200 mM, or from about 20 mM to about 150 mM, or from about 50 mM to about 100 mM.

The disclosure includes embodiments in which the pH of the neurosteroid nanoparticle formulation is about 7.4.

The formulation may contain electrolytes, such as sodium or potassium. The disclosure includes embodiments in which the formulation is from about 0.5% to about 1.5% sodium chloride (saline).

The formulation may contain tonicity adjusting agents so that it is isotonic with human plasma. Examples of tonicity adjusting agents useful in the formulation include, but are not limited to, dextrose, mannitol, sodium chloride, or glycerin. In certain embodiments the tonicity agent is 0.9% sodium chloride.

The injectable neurosteroid nanoparticle formulations may contain any pharmaceutically acceptable excipient compatible with the neurosteroid and capable of providing the desired pharmacological release profile for the dosage form. Excipients include, for example, suspending agents, surfactants, solubilizers, stabilizers, lubricants, wetting agents, anti-foaming agent, diluents, and the like. Pharmaceutically acceptable excipients may comprise, but are not limited to, acacia, gelatin, colloidal silicon dioxide, calcium glycerophosphate, calcium lactate, maltodextrin, glycerin, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

Suitable antifoaming agents include dimethicone, myristic acid, palmitic acid, and simethicone.

The injectable neurosteroid nanoparticle formulation may also contain a non-aqueous diluent such as ethanol, one or more polyol (e.g. glycerol, propylene glycol), an oil carrier, or any combination of the foregoing.

The injectable neurosteroid nanoparticle formulation may additionally comprise a preservative. The preservative may be used to inhibit bacterial growth or prevent deterioration of the active agent. Preservatives suitable for parenteral formulations include ascorbic acid, acetylcysteine, benzalkonium chloride, benzethonium chloride, benzoic acid, benzyl alcohol, chlorbutanol, chlorhexidene, m-cresol, 2-ethoxyethanol, human serum albumin, monothioglycerol, parabens (methyl, ethyl, propyl, butyl, and combinations), phenol, phenylmercurate salts (acetate, borate nitrate), sorbic acid, sulfurous acid salts (bisulfite and metabisulfite), and thimerosal. In certain embodiments the preservative is an antioxidants such ascorbic acid, glutathione, or an amino acid. Amino acids useful as antioxidants include methionine, cysteine, and L-arginine.

Lyophilized Neurosteroid Nanoparticle Formulations

The disclosure includes lyophilized forms of all formulations disclosed herein.

The injectable neurosteroid nanoparticle formulations provided in this disclosure are aqueous formulations or powder formulations including lyophilized forms, which may be readily resuspended in water to provide an injectable formulation. The disclosure includes embodiments in which the lyophilized neurosteroid powder comprises the neurosteroid, a surface stabilizer such as either hydroxyethyl starch or dextran, and a surfactant, wherein the injectable formulation is about 0.5% to about 40% neurosteroid, about 0.5% to about 20% neurosteroid, about 0.5% to about 10% neurosteroid, about 0.5% to about 2.0%, or about 1.0% to about 1.5% weight neurosteroid.

The disclosure provides injectable neurosteroid nanoparticle formulations containing neurosteroid nanoparticles containing neurosteroid and an excipient, such as hydroxy ethyl starch or dextran, and optionally a surfactant. In certain embodiments the neurosteroid nanoparticle formulation is a lyophilized form that is dissolved in water or an aqueous solution prior to administration.

The lyophilized form may additionally include an antifoaming agent, a buffer (or pH adjuster), a cryoprotectant, a bulking agent, a tonicity adjuster, or a combination of any of the foregoing.

Bulking agents are useful for lyophilized formulation in which a low concentration of the active ingredient, or in the present case, in which a low concentration of the inclusion complex, is present. Bulking agents include mannitol, lactose, sucrose, trehalose, sorbitol, glucose, rafinose, glycine, histidine, polyethylene glycol (PEG), and polyvinyl pyrrolidone (PVP).

The removal of the hydration shell from an active agent during lyophilization can be destabilizing. In certain embodiments the lyophilized form contains a stabilizer which serves as a cryoprotectant. Stabilizers include agents which maintain a desirable attribute of the formulation over a time interval including but not limited to mechanical, chemical and temperature stressing that can be tested in a laboratory setting. Such attributes include stable particle size or homogeneity resulting in concentrations consistent with the labeled potency and maintaining purity.

Suitable cryoprotectant stabilizers include sugars such as sucrose, trehalose, glucose, rafinose, lactose, mannitol, sorbitol, histidine, polyethylene glycol (PEG), and polyvinyl pyrrolidone and sodium chloride.

Ebeam Sterilized Nanoparticulate Formulations

Electron beam sterilization (ebeam) is a process using beta radiation, usually of high energy, to effect sterilization of a sample. Surprisingly, it has been determined that the injectable nanoparticle neurosteroid formulations of this disclosure can be sterilized with ebeam radiation without affecting particle size, impurity levels or viscosity. Lyophilized powders of the injectable nanoparticle neurosteroid formulations may also be sterilized with ebeam radiation without adverse effects.

Additional embodiments of the disclosure include injectable nanoparticle neurosteroid formulations sterilized with ebeam irradiation. Lyophilized powders or other dry forms of such formulations are also included in this disclosure. The injectable nanoparticle neurosteroid formulations of this disclosure can be subjected to ebeam irradiation, preferably at ambient temperature. This temperature remains relatively constant during irradiation.

The ebeam radiation is applied in an amount sufficient to destroy substantially all of the microbial contamination in the dispersion. The total amount of ebeam radiation that dispersion is exposed to has been experimentally verified to: (1) show only a modest increase in particle size on storage following exposure to ebeam irradiation, (2) maintain the integrity of the nanoparticulate active agent, and (3) to show acceptable impurity concentrations following ebeam irradiation. The application of the ebeam radiation does not significantly degrade the neurosteroid or reduce its efficacy. The present disclosure enables products which meet cGMP requirements for sterile products without harming the neurosteroid nanoparticles.

In certain embodiments the ebeam radiation is applied in a cumulative amount of 25 kGray. Generally, the ebeam radiation will normally be applied in a range of 5 kGray to 50 kGray, 5 kGray to 40 kGray, 10 kGray to 30 kGray, 5 to 15 kGray, or 5 to 10 kGray. Multiple doses of radiation can be utilized to achieve a desired cumulative radiation dosage.

The microbial contamination which is to be destroyed is generally that of bacterial contamination and mycoplasma contamination.

Surprisingly, following sterilization the injectable neurosteroid nanoparticle formulations exhibit unexpected overall stability, maintaining the pre-sterilized physical and chemical properties, while meeting cGMP requirements for sterility. The overall stability of the ebeam irradiated dispersions of nanoparticulate neurosteroid was measured in terms of neurosteroid nanoparticle particle size, content of degradation products, and viscosity. It is particularly unexpected that ebeam irradiation of the injectable neurosteroid nanoparticle formulations does not significantly alter the particle size of the neurosteroid nanoparticles. This is significant because if the sterilized product formed aggregates or large crystals, the dispersion would no longer be useful as an injectable formulation. Other means of sterilization including heat sterilization were found to alter the neurosteroid nanoparticle particle size.

Methods of Treatment

The disclosure includes methods of treating status epilepticus, refractory status epilepticus, super-refractory status epilepticus, PCDH19 female pediatric epilepsy, and other seizure disorders comprising administering an effective amount of the neurosteroid nanoparticle injectable formulation to a patient suffering from any of these seizure disorders.

Seizure disorders that may be treated with the neurosteroid nanoparticle injectable formulation include status epilepticus, e.g., convulsive status epilepticus, e.g., early status epilepticus, established status epilepticus, refractory status epilepticus, super-refractory status epilepticus, e.g., super-refractory generalized status epilepticus; non-convulsive status epilepticus, e.g., generalized status epilepticus, complex partial status epilepticus; a seizure, e.g., acute repetitive seizures, cluster seizures, infantile spasms, Lennox-Gastaut syndrome, West syndrome, PCDH19 female pediatric epilepsy, and catamenial epilepsy.

The neurosteroid nanoparticle injectable formulation may also be used to treat provoked seizures such as seizures resulting from low blood sugar, electrolyte imbalance, high fever, brain infection (such as brain infections due to encephalitis, malaria, meningitis, toxoplasmosis, or amoebic infection), adverse reaction to prescription drugs, or alcohol or drug overdose.

The disclosure also includes methods of using neurosteroid nanoparticle injectable formulation to treat traumatic brain injury and stroke comprising administering an effective amount of the formulation to a patient suffering from recent traumatic brain injury or a recent stroke.

The disclosure further includes methods of treating seizures arising from neurodegenerative disorders. Such neurodegenerative disorders include Parkinson's disease, Alzheimer's disease, Amyotrophic Lateral Sclerosis, and Huntington's disease. The disclosure includes methods of treating seizure arising from inflammatory disorders, such as multiple sclerosis. The disclosure includes methods of treating seizure disorders arising from lysosomal storage disorders including Neimann-Pick-C, Tay Sachs, Batten, Sandhoff, and Gaucher disease.

Methods of treatment include treating a patient suffering from seizures, traumatic brain injury, or stroke by administering a single injection (bolus dose) of a neurosteroid nanoparticle injectable formulation. The single injection may be administered intramuscularly or intravenously. The dose of the single injection may be from about 0.5 mg/kg to about 20 mg/kg, from about 2 mg/kg to about 15 mg/kg, from about 2 mg/kg to about 10 mg/kg, or about 2 mg/kg to about 8 mg/kg. Methods of treatment also include administering multiple injections of the neurosteroid nanoparticle injectable formulation over a period of 1 to 10 days. The injections may be given at intervals of 1 to 24 hours. Dosing schedules in which the injectable neurosteroid nanoparticle formulation is injected every 1 hour. 2 hours. 4 hours, 6 hours, 8 hours, 12 hours, or 24 hours are included herein. Dosing schedules in which the neurosteroid nanoparticle injectable formulation is injected for 1, 2, 3, 4, 5, 6, 7, 8, 9, or 10 days are included herein.

Methods of treatment include treating a patient suffering from seizures, traumatic brain injury, or stroke by administering one or more bolus doses over a period of 1 to 10 days as described in the preceding paragraph of a neurosteroid nanoparticle injectable formulation followed by an intravenous infusion of the neurosteroid nanoparticle injectable formulation. In certain embodiments the bolus dose is administered over a period of about 1 to about 30, about 1 to about 15, about 1 to about 10, or about 1 to about 5, or about 5 minutes followed by commencement of the intravenous infusion within 1, 2, 3, 4, or 5 hours.

In some embodiments, neurosteroid nanoparticle injectable formulation is administered as an intravenous infusion dose, either with or without a previous bolus dose for 1, 2, 3, 4, 5, 6, 7, 8, 9, or 10 consecutive days. The infusion dose may be administered at a rate of 1, 2, 3, 4, 5, 6, 7, 8, 9, or 10 mg/kg/hr or in a range of about 1 mg/kg/hr to about 10 mg/kg/hr or 2 mg/kg/hr to about 8 mg/kg/hrs.

In some embodiments the infusion dose (whether administered with or without the bolus dose) is followed by a first step down dosage, and optionally a second step down dosage, an optionally a third step down infusion dosage. In some embodiments, the first step dose is 95%, 90%, 85%, 80%, 75%, 70%, 65%, 60%, 55%, 50%, 45%, 40%, 35%, 30%, 25%, 20%, 15%, 10%, or 5% of the infusion dose. In some embodiments, the first step dose is between 95-50%, 75-50%, 85-50%, 90-50%, 80-50%, or 75-100% of the infusion dose. In an embodiment, the first step dose is 75% of the infusion dose. In some embodiments, the second step dose is 95%, 90%, 85%, 80%, 75%, 70%, 65%, 60%, 55%, 50%, 45%, 40%, 35%, 30%, 25%, 20%, 15%. 10%, or 5% of the first step down dose. In some embodiments, the second step dose is between 95-30%, 75-30%, 85-30%, 60-30%, 70-30%, 50-30%, or 50-40% of the first step down dose. In an embodiment, the second step dose is 50% of the infusion dose. In some embodiments, the third step dose is 95%, 90%, 85%, 80%, 75%, 70%, 65%, 60%, 55%. 50%, 45%, 40%, 33%, 30%, 25%, 20%, 15%, 10%, or 5% of the second infusion dose. In some embodiments, the third step dose is between 50-5%, 40-5%, 30-5%, 25-5%, 25-10%, 25-20%, or 25-40% of the second step down dose. In an embodiment, the third step down dose is 25% of the infusion dose.

The disclosure includes methods of treating a seizure disorder wherein the seizure disorder is status epilepticus, refractory status epilepticus, super refractory status epilepticus, or PCDH19 female pediatric epilepsy comprising administering an effective amount of the neurosteroid nanoparticle injectable formulation to a patient.

The disclosure includes methods of treating a seizure disorder, stroke, or traumatic brain injury, comprising administering an effective amount of the neurosteroid nanoparticle injectable formulation to a patient wherein the amount of neurosteroid administered is from about 1 mg/kg to about 200 mg/kg.

In certain embodiments the neurosteroid nanoparticle injectable formulation is administered intramuscularly or intravenously.

The disclosure includes embodiments in which the neurosteroid nanoparticle injectable formulation is administered as a single bolus dose of the neurosteroid formulation to the patient. In certain embodiments the single bolus dose provides a sufficient amount of neurosteroid to provide a plasma $C_{max}$ of neurosteroid of about 100 ng/mL to about 1000 ng/mL in the patient.

The disclosure includes embodiments in which the neurosteroid nanoparticle injectable formulation is administered as a bolus dose and the bolus dose provides a sufficient amount of neurosteroid to provide a plasma $C_{max}$ of neurosteroid of about 100 ng/mL to about 800 ng/mL in the patient.

The disclosure includes embodiments in which the neurosteroid nanoparticle formulation is administered as a bolus dose and the bolus dose is administered in less than 10 minutes and the $C_{max}$ occurs within 1 hour of completion of administration.

The disclosure includes embodiments in which the neurosteroid nanoparticle formulation is administered as a single bolus dose and the single bolus dose comprises from about 0.5 mg/kg to about 20 mg/kg neurosteroid. Or, optionally the single bolus dose comprises from about 2 mg/kg to about 15 mg/kg neurosteroid, or about 4 mg/kg to about 10 mg/kg neurosteroid, or from about 1 mg/kg to about 30 mg/kg neurosteroid.

The disclosure includes embodiments in which multiple bolus doses of the neurosteroid nanoparticle formulation are administered to the patient. In certain embodiments the multiple bolus doses are given over 1 to 10 days at intervals of 1 to 24 hours. In certain embodiments each bolus dose provides a sufficient amount of neurosteroid to produce a plasma $C_{max}$ of neurosteroid of about 100 ng/mL to about 8000 ng/mL in the patient. In certain embodiments the interval between bolus doses is from about 10 to about 24 hours and once an initial $C_{max}$ is reached the plasma concentration of neurosteroid is not below 100 ng/mL at any time between bolus doses. In certain embodiments the interval between bolus doses is 20 to 24 hours and once an initial $C_{max}$ is reached and the concentration of neurosteroid in the patient's plasma does not fall below 25% of the initial $C_{max}$. In certain embodiment each bolus dose comprises about 1 mg/kg to about 20 mg/kg neurosteroid. Or, optionally the single bolus dose comprises from about 2 mg/kg to about 15 mg/kg neurosteroid, or about 4 mg/kg to about 10 mg/kg neurosteroid, or from about 1 mg/kg to about 30 mg/kg neurosteroid.

In certain embodiments the method comprises administering an infusion of the neurosteroid nanoparticle formulation to the patient, with or without an initial bolus dose. In certain embodiments the infusion is administered for 1 to 10 consecutive days at a rate of 1 to 10 mg/kg/hr without an initial bolus dose.

In certain embodiments the method comprises administering an initial bolus dose of the neurosteroid nanoparticle injectable formulation comprising from about 1 mg/kg to about 20 mg/kg neurosteroid, followed within 24 hours by administration of an infusion of the neurosteroid formulation for 1 to 10 consecutive days at a rate of 1 to 10 mg/kg/hr.

In certain embodiments the method comprises administering an initial bolus dose of the neurosteroid nanoparticle injectable formulation followed by an infusion dose, wherein the initial bolus dose provides a sufficient amount of neurosteroid to provide an initial plasma $C_{max}$ of neurosteroid of about 100 ng/mL to about 1000 ng/mL in the patient and the concentration of neurosteroid in the patient's plasma does not fall below 25% of the initial $C_{max}$ until after the subsequent infusion dosing is concluded.

In certain embodiments the method comprises administering an initial bolus dose of the neurosteroid nanoparticle injectable formulation, wherein the initial bolus dose provides a sufficient amount of neurosteroid to provide an initial plasma $C_{max}$ of neurosteroid of about 100 ng/mL to about 8000 ng/mL in the patient, the patient is then administered an infusion of the neurosteroid formulation at a constant dose sufficient to provide a concentration of neurosteroid in the patient's plasma of at least 40% of $C_{max}$, followed by an infusion of neurosteroid at a gradually reducing dose so that the concentration of neurosteroid in the patient's plasma is less than 20% of $C_{max}$ when the infusion is concluded.

Combination Treatment

The disclosure includes embodiments in which the neurosteroid is the only active agent and embodiments in which the neurosteroid is administered in combination with one or more additional active agents. When used in combination with an additional active agent the neurosteroid and the additional active agent may be combined in the same formulation or may be administered separately. The neurosteroid may be administered while the additional active agent is being administered (concurrent administration) or may be administered before or after the additional active agent is administered (sequential administration).

The disclosure includes embodiments in which the additional active agent is an anti-convulsant. Anticonvulsants include GABAA receptor modulators, sodium channel blocker, GAT-1 GABA transporter modulators, GABA transaminase modulators, voltage-gated calcium channel blockers, and peroxisome proliferator-activated alpha modulators.

The disclosure includes embodiments in which the patient is given an anesthetic or sedative in combination with a neurosteroid. The anesthetic or sedative may be administered at a concentration sufficient to cause the patient to lose consciousness, such as a concentration sufficient to medically induce coma or a concentration effective to induce general anesthesia. Or the anesthetic or sedative may be given at a lower dose effective for sedation, but not sufficient to induce a loss of consciousness.

A medically induced coma occurs when a patient is administered a dose of an anesthetic, such as propofol, pentobarbital or thiopental, to cause a temporary coma or a deep state of unconsciousness. General anesthesia is a treatment with certain medications to cause unconsciousness sufficient to be unaware of pain during surgery. Drugs used for medically induced coma or general anesthesia include inhalational anesthetics and intravenous anesthetics which include barbiturate and non-barbiturate anesthetics.

Inhalational anesthetics include desflurane, enflurane, ethyl chloride, halothane, isoflurane, methoxyflurane, sevoflurane, and trichloroethylene.

Intravenous, non-barbiturate anesthetics include atracurium, cisatracurium, etodimidate, ketamine, propofol, and rocuronium, Barbiturates include amobarbital, methohexital, pentobarbital, phenobarbital, secobarbital, thiamylal, and thiopental.

Benzodiazepines are used both as anticonvulsants and anesthetics. Benzodiazepines useful as anaesthetics include diazepam, flunitrazepam, lorazepam, and midazolam.

The disclosure includes administering propofol to induce anesthesia in combination with a neurosteroid. Propofol is administered at a dose range or dosage range of 0.5-50 mg/kg. Anesthesia is induced with an initial bolus of 10-50 mg/kg followed by additional intermittent boluses or 10-50 mg/kg to maintain anesthesia. Anesthesia may also be maintained by an infusion of 3-18 mg/kg/min propofol.

The disclosure includes administering pentobarbital sodium by intravenous or intramuscular injection to induce anesthesia in combination with a neurosteroid. Pentobarbital may be administered to adults as a single 100-500 mg, or 100-200 mg intramuscular or intravenous injection, or to pediatric patients as a single 2 to 6 mg/kg IM or IV injection. Pentobarbital may be administered at a high dose to induce coma in a status epilepticus patient and a neurosteroid may then be given in combination with the pentobarbital to treat refractory seizures. Pentobarbital doses used to induce coma include, a loading dose of 5 to 15 mg/kg or 10 to 35 mg/kg, given over 1-2 hours followed by a maintenance dose of 1 mg/kg/hr to 5 mg/kg/hr for 12 to 48 hours and tapering by 0.25 to 0.5 mg/kg/hr every 12 hours once seizures have stopped.

The disclosure includes administering thiopental sodium in combination with a neurosteroid. Thiopental can be administered as a 3 to 5 mg/kg bolus followed by additional boluses of 1 to 2 mg/kg every 3 to 5 minutes until seizures have stopped, to a maximum total dose of 10 mg/kg. After the 10 mg/kg maximum bolus dose of thiopental has been reached, thiopental can be infused at 3 to 5 mg/kg/hr.

The disclosure includes administering midazolam in combination with a neurosteroid. Midazolam can be administered as a 0.5 mg/kg to 5 mg/kg loading dose, followed by a 1 to 5 microgram/kg/hour infusion.

In each embodiment in which an additional active agent is administered to induce coma, anesthesia, or sedation, a neurosteroid is administered as a neurosteroid nanoparticle injectable formulation and is administered simultaneously or sequentially with the additional active agent and is administered according to any of the dosing schedules set forth herein for neurosteroid administration.

The neurosteroid nanoparticle injectable formulation of this disclosure may be administered with another anticonvulsant agent. Anticonvulsants include a number of drug classes and overlap to a certain extent with the coma-inducing, anesthetic, and sedative drugs that may be used in combination with a neurosteroid. Anticonvulsants that may be used in combination with the neurosteroid nanoparticle injectable formulation of this disclosure include aldehydes, such as paraldehyde; aromatic allylic alcohols, such as stiripentol, barbiturates, including those listed above, as well as methylphenobarbital and barbexaclone; benzodiazepines include alprazolam, bretazenil, bromazepam, brotizolam, chloridazepoxide, cinolazepam, clonazepam, chorazepate, clopazam, clotiazepam, cloxazolam, delorazepam, diazepam, estazolam, etizolam, ethyl loflazepate, flunitrazepam, flurazepam, flutoprazepam, halazepam, ketazolam, loprazolam, lorazepam, lormetazepam, medazepam, midazolam, nimetazepam, nitrazepam, nordazepam, oxazepam, phenenazepam, pinazepam, prazepam, premazepam, pyrazolam, quazepam, temazepam, tatrazepam, and triazolam; bromides, such as potassium bromide; carboxamides, such carbamazepine, oxcarbazepine, and eslicarbazepine acetate; fatty acids, such as valproic acid, sodium valproate and divalproex sodium; fructose derivatives, such as topiramate; GABA analogs such as gabapentin and pregabalin, hydantoins, such as ethotoin, phenytoin, mephenytoin, and fosphenytoin; other neurosteroids, such as allopregnanolone, oxasolidinediones, such as paramethadione, trimethadione, and ethadione, propionates such as beclamide; pyrimidinediones such as primidone, pyrrolidines such as brivaracetam, levetiracetam, and seletracetam, succinimides, such as ethosuximide, pensuximide, and mesuximide; sulfonamides such as acetazoloamide, sultiame, methazolamide, and zonisamide; triazines such as lamotrigine, ureas such as pheneturide and phenacemide, NMDA antagonists, such as felbamate, and valproylamides such as valpromide and valnoctamide; and perampanel.

Specific Embodiments

The disclosure provides the following specific embodiments that are further illustrated by the examples that follow.

(1) An injectable neurosteroid formulation comprising nanoparticles having a D50 of less than 2000 nm, the nanoparticles comprising a) a neurosteroid of the Formula I:

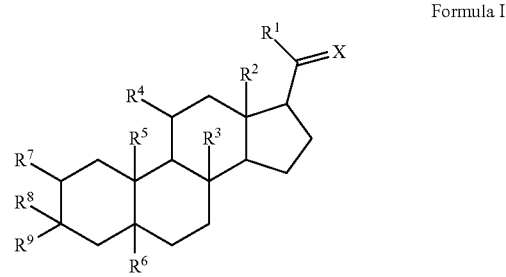

Formula I or a pharmaceutically acceptable salt thereof, wherein:

X is O, S, or $N^{10}$;

$R^1$ is hydrogen, hydroxyl, optionally substituted alkyl, optionally substituted heteroalkyl, optionally substituted aryl, or optionally substituted arylalkyl;

$R^4$ is hydrogen, hydroxyl, oxo, optionally substituted alkyl, or optionally substituted hetero alkyl, $R^2$, $R^3$, $R^5$, $R^6$, and $R^7$ are each independently hydrogen, hydroxyl, halogen, optionally substituted alkyl, or optionally substituted heteroalkyl;

$R^8$ is hydrogen or alkyl and $R^9$ is hydroxyl; or $R^8$ and $R^9$ are taken together to form an oxo group;

$R^{10}$ is hydrogen, hydroxyl, optionally substituted alkyl, optionally substituted heteroalkyl, optionally substituted aryl, or optionally substituted arylalkyl where each alkyl is a $C_1$-$C_{10}$alkyl, $C_3$-$C_6$cycloalkyl, ($C_3$-$C_6$cycloalkyl)$C_1$-$C_4$alkyl, and optionally contains a single bond replaced by a double or triple bond;

each heteroalkyl group is an alkyl group in which one or more methyl group is replaced by an independently chosen —O—, —S—, —N($R^{10}$)—, —S(=O)— or —S(=O)$_2$—, where $R^{10}$ is hydrogen, alkyl, or alkyl in which one or more methylene group is replaced by —O—, —S—, —NH, or —N-alkyl; and (b) at least one surface stabilizer.

(2) The injectable neurosteroid formulation of Specific Embodiment 1, wherein

X is O;

$R^1$ is $C_1$-$C_2$alkyl optionally substituted with hydroxyl;

$R^2$ and $R^5$ are methyl;

$R^3$ and $R^6$ are hydrogen;

$R^4$ is hydrogen, $C_1$-$C_2$alkyl, mono- or di-$C_1$-$C_2$alkylamino, or oxo;

$R^7$ is hydrogen, $C_1$-$C_2$alkyl, or $C_1$-$C_2$alkoxy; and $R^8$ is hydrogen or methyl and $R^9$ is hydroxyl; or $R^8$ and $R^9$ are taken together to form an oxo group.

(3) The injectable neurosteroid formulation of Specific Embodiment 2, wherein $R^4$ is hydrogen or oxo; and $R^8$ is hydrogen or methyl and $R^9$ is hydroxyl.

(4) The injectable neurosteroid formulation of any one of Specific Embodiments 1 to 3, wherein the formulation is an intravenous formulation. The injectable neurosteroid formulation of any one of Specific Embodiments 1 to 3, wherein the formulation is an intramuscular formulation. The injectable neurosteroid formulation of any one of Specific Embodiments 1 to 3, wherein the formulation is a subcutaneous formulation.

(5) The injectable neurosteroid formulation of Specific Embodiments 1 to 4, wherein the neurosteroid is allopregnanolone, ganaxolone, alphaxalone, alphadolone, hydroxydione, minaxolone, pregnanolone, or tetrahydrocorticosterone.

(6) The injectable neurosteroid formulation of Specific Embodiment 5, wherein the neurosteroid is ganaxolone or allopregnanolone.

(7) The injectable neurosteroid formulation of Specific Embodiment 6, wherein the neurosteroid is ganaxolone.

(8) The injectable neurosteroid formulation of Specific Embodiment 6, wherein the neurosteroid is allopregnanolone.

(9) The injectable neurosteroid formulation of any one of Specific Embodiments 1 to 8 wherein the nanoparticles have a D50 of less than 500 nm.

(10) The injectable neurosteroid formulation of Specific Embodiment 9, wherein the nanoparticles have a D90 of less than 500 nm.

(11) The injectable neurosteroid formulation of Specific Embodiment 9 wherein the nanoparticles have a D50 of 10 nm to 300 nm.

(12) The injectable neurosteroid formulation of any one of Specific Embodiments 1 to 11, wherein the at least one surface stabilizer is a polymeric surface stabilizer.

(13) The injectable neurosteroid formulation of Specific Embodiment 12, wherein the polymeric surface stabilizer is hydroxyethyl starch, dextran, povidone, or a mixture of any of the foregoing.

(14) The injectable neurosteroid formulation of Specific Embodiment 13, wherein the surface stabilizer is hydroxyethyl starch. (Such as hydroxyethyl starch 130/0.4)

(15) The injectable neurosteroid formulation of Specific Embodiment 13, wherein the surface stabilizer is dextran having an average molecular weight of 40 kD to 75 kD.

(16). The injectable neurosteroid formulation of Specific Embodiment 15, wherein the dextran is Dextran 70.

(17) The injectable neurosteroid formulation of Specific Embodiment 13, wherein the surface stabilizer is povidone. (Such as plasdone C-12 or plasdone C-17)

(18). The injectable neurosteroid formulation of any one of Specific Embodiments 1 to 17, wherein the formulation comprises an additional surface stabilizer and the additional surface stabilizer is an ionic or nonionic surfactant.

(19) The injectable neurosteroid formulation of Specific Embodiment 18, wherein the surfactant is sodium cholate, sodium deoxycholate, sodium cholesterol sulfate, or a mixture of any of the foregoing.

(20). The injectable neurosteroid formulation of Specific Embodiment 19, wherein the surfactant is sodium deoxycholate.

(21) The injectable neurosteroid formulation of any one of Specific Embodiments 1 to 20, wherein the formulation additionally comprises an antifoaming agent.

(22) The injectable neurosteroid formulation of Specific Embodiment 21, wherein the antifoaming agent is simethicone.

(23) The injectable neurosteroid formulation of any one of Specific Embodiments 1 to 22 additionally comprising a cryoprotectant.

(24) The injectable neurosteroid formulation of Specific Embodiment 23, wherein the cryoprotectant is sucrose, dextrose, lactose, D-sorbitol, or a mixture of any of the foregoing.

(25) The injectable neurosteroid formulation of Specific Embodiment 24, wherein the cryoprotectant is sucrose.

(26) The injectable neurosteroid formulation of any one of Specific Embodiments 1 to 25, wherein the formulation additionally comprises 0.5% to 1.5% sodium chloride (weight percent).

(27) The injectable neurosteroid formulation of Specific Embodiment 27, wherein the formulation comprises about 0.9% sodium chloride.

(28) The injectable neurosteroid formulation of any one of Specific Embodiments 1 to 27, additionally comprising a buffer.

(29) The injectable neurosteroid formulation of Specific Embodiment 28, wherein the buffer is a phosphate buffer.

(30) The injectable neurosteroid formulation of Specific Embodiment 29, wherein the buffer is phosphate buffered saline.

(31) The injectable neurosteroid formulation of any one of Specific Embodiments 1 to 30, additionally comprising a preservative.

(32) The injectable neurosteroid formulation of Specific Embodiment 31, wherein the preservative is benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal, a phenylmercurate salt, or a mixture of any of the foregoing.

(33) The injectable neurosteroid formulation of any one of the foregoing embodiments, wherein
the neurosteroid is ganaxolone or allopregnanolone,
the at least one surface stabilizer is a polymeric surface stabilizer selected from hydroxyethyl starch, dextran, povidone, or a mixture of the foregoing, and
the formulation comprises and additional surface stabilizer and the additional surface stabilizer is a surfactant chosen from sodium deoxycholate or sodium cholesterol sulfate and the (wt:wt) ratio of the neurosteroid to the surface stabilizer is about 10:1 to about 1:1. (34) The injectable neurosteroid formulation of Specific Embodiment 33 wherein the (wt:wt) ratio of the neurosteroid to the polymeric surface stabilizer is about 4:1 to about 3:1.

(35) The injectable neurosteroid formulation of Specific Embodiment 34 wherein the (wt:wt) ratio of the neurosteroid to the polymeric surface stabilizer is about 3.3:1.

(36) The injectable neurosteroid formulation of any one of Specific Embodiment 1 to 35, wherein the ratio of neurosteroid to surfactant (w:w) is about 10:1.5 to about 10:0.1.

(37) The injectable neurosteroid formulation of any one of Specific Embodiments 23 to 36, wherein the ratio (w:w) of neurosteroid to cryoprotectant is 4:1 to 1:4.

(38) The injectable neurosteroid formulation of any one of Specific Embodiments claims 1 to 37, wherein the formulation is in the form of a lyophilized powder.

(39) The injectable neurosteroid formulation any one of Specific Embodiments 1 to 37, wherein the formulation is an aqueous suspension and the neurosteroid concentration is about 0.1 mg/mL to about 300 mg/mL.

(40) The injectable neurosteroid formulation of any one of Specific Embodiments 1 to 37 or 39, wherein the weight percent of neurosteroid is from about 0.1% to about 30% and the neurosteroid is ganaxolone or allopregnanolone.

(41) The injectable neurosteroid formulation of Specific Embodiment 40, wherein the weight percent of ganaxolone or allopregnanolone is from about 0.5% to about 2.0%.

(42) The injectable neurosteroid formulation of any one of Specific Embodiments 23 to 42, wherein the weight percent of cryoprotectant in the formulation is from about 5% to about 60%.

(43) The injectable neurosteroid formulation of Specific Embodiment 42, wherein the weight percent of cryoprotectant in the formulation is from about 10% to about 40%.

(44). The injectable neurosteroid formulation of any one of Specific Embodiments 1 to 43, having a pH in the range of approximately 2.5-11.0.

(45) The injectable neurosteroid formulation of Specific Embodiment 44, having a pH of about 7.0 to about 7.6.

(46) The injectable neurosteroid formulation of Specific Embodiment 1, wherein the formulation is an aqueous formulation comprising
(a) nanoparticles having a D50 of less than 500 nm, the nanoparticles comprising ganaxolone, wherein the weight percent of the ganaxolone is 1 to 10%;
(b) a polymeric surface stabilizer is hydroxyethyl starch, dextran, povidone, or a mixture of any of the foregoing, wherein the weight percent of the polymeric surface stabilizer is 2 to 20%
(c) an additional surface stabilizer wherein the additional surface stabilizer is an ionic or nonionic surfactant selected sodium cholate, sodium deoxycholate, sodium cholesterol sulfate, wherein the weight percent surfactant is 0.1% to 2.0%; and
(d) an antifoaming agent.

(47) The injectable neurosteroid formulation of Specific Embodiment 1 wherein the formulation is an aqueous formulation comprising
(a) nanoparticles having a D50 of less than 500 nm, the nanoparticles comprising ganaxolone, wherein the weight percent of the ganaxolone is about 5%;
(b) a polymeric surface stabilizer selected from hydroxyethyl starch 130/0.4 or plasdone C-12, wherein the weight percent of the polymeric surface stabilizer is about 10%;
(c) an additional surface stabilizer wherein the additional surface stabilizer is sodium deoxycholate, wherein the weight percent of sodium deoxycholate is about 0.75% and
(d) simethicone, wherein the weight percent of simethicone is 0.009%. (48) A method for sterilizing the injectable neurosteroid nanoparticle formulation of any one of Specific Embodiments 1 to 47, comprising subjecting the formulation to ebeam radiation, wherein the method produces a sterilized neurosteroid nanoparticle formulation containing a degradant concentration of not more than 0.2% w/w of neurosteroid.

(49) The injectable neurosteroid formulation of any one of Specific Embodiments 1 to 47, wherein the formulation has been sterilized by ebeam irradiation and wherein the formulation contains a degradant concentration of not more than 0.2% w/w of the neurosteroid.

(50) The injectable neurosteroid formulation of Specific Embodiment 49, wherein the ebeam irradiation is a cumulative dose of about 25 kGray.

(51) The injectable neurosteroid formulation of Specific Embodiment 50, wherein the ebeam irradiation is a dose selected from 5 kGray to 50 kGray, 5 kGray to 30 kGray, 5 kGray to 25 kGray, 5 kGray to 20 kGray, 5 kGray to 15 kGray, and 5 kGray to 10 kGray.

(52) An injectable ganaxolone nanoparticulate formulation comprising:
(a) ganaxolone nanoparticles having a D50 of 2000 nm or less and (b) at least one surface stabilizer;
wherein in comparative pharmacokinetic testing with an injectable non-particulate ganaxolone formulation of the same dosage strength the nanoparticulate formulation exhibits a greater $C_{max}$ than the non-particulate ganaxolone formulation.

(53) An injectable ganaxolone nanoparticulate formulation comprising:
(a) ganaxolone nanoparticles having a D50 of 2000 nm or less and (b) at least one surface stabilizer;
wherein in comparative pharmacokinetic testing with an injectable non-particulate ganaxolone formulation of the same dosage strength the nanoparticulate formulation exhibits a greater brain $AUC_{6\ hrs}$ than the non-particulate ganaxolone formulation.

(54) An injectable ganaxolone nanoparticulate formulation comprising:
(a) ganaxolone nanoparticles having a D50 of 2000 nm or less and (b) at least one surface stabilizer;
wherein in comparative pharmacokinetic testing with an injectable non-particulate ganaxolone formulation of the same dosage strength the nanoparticulate formulation exhibits a greater brain concentration at any time from 15 to 100 minutes after administration than the non-particulate ganaxolone formulation exhibits at the same time after administration.

(55). A method of treating a patient having a seizure disorder, stroke, or traumatic brain injury, the method comprising administering a therapeutically effective amount of the injectable neurosteroid formulation of any one of the preceding Specific Embodiments.

(56) The method of Specific Embodiment 55, wherein the seizure disorder is status epilepticus, refractory status epilepticus, super refractory status epilepticus, or PCDH19 female pediatric epilepsy.

(57) The method of Specific Embodiment 55 or 56 wherein the neurosteroid is ganaxolone or allopregnanolone and the dosage of neurosteroid administered is from about 1 mg/kg to about 200 mg/kg.

(58) The method of Specific Embodiment of any one of Specific Embodiment 55 to 57, wherein the neurosteroid is ganaxolone.

(59) The method of any one of Specific Embodiments 55 to 58 wherein the formulation is administered intravenously. The method of any one of Specific Embodiments 55 to 58 wherein the formulation is administered intramuscularly.

(60) The method of Specific Embodiment 59 comprising administering a single bolus dose of the formulation to the patient.

(61) The method of Specific Embodiment 60 wherein the single bolus dose provides a sufficient amount of ganaxolone to provide a plasma $C_{max}$ of ganaxolone of at least 1000 ng/mL in the patient.

(62) The method of Specific Embodiment 61, wherein the bolus dose provides a sufficient amount of ganaxolone to provide a plasma $C_{max}$ of ganaxolone of about 1000 ng/mL to about 6000 ng/mL in the patient.

(63) The method of Specific Embodiment 60 or 61, wherein the bolus dose is administered in less than 10 minutes and $C_{max}$ occurs within 1 hour of completion of administration.

(64) The method of any one of Specific Embodiment 60 to 63, wherein the single bolus dose comprises from about 1 mg/kg to about 20 mg/kg ganaxolone.

(65). The method of any one of Specific Embodiments 55 to 59 comprising administering multiple bolus doses of the ganaxolone formulation to the patient.

(66) The method of Specific Embodiment 65 wherein the multiple bolus doses are given over 1 to 10 days at intervals of 1 to 24 hours.

(67) The method of Specific Embodiment 65 wherein each bolus dose provides a sufficient amount of ganaxolone to produce a plasma $C_{max}$ of ganaxolone of at least 1000 ng/mL in the patient.

(68) The method of Specific Embodiment 65, wherein the interval between bolus doses is from about 10 to about 24 hours and once an initial $C_{max}$ is reached the plasma concentration of ganaxolone is not below 100 ng/mL at any time between bolus doses.

(69) The method of Specific Embodiment 65, wherein the interval between bolus doses is from about 20 to about 24 hours and once an initial $C_{max}$ is reached the concentration of ganaxolone in the patient's plasma does not fall below 25% of the initial $C_{max}$ at any time between bolus doses.

(70) The method of any one of Specific Embodiments 65 to 69 wherein each bolus dose comprises about 1 mg/kg to about 20 mg/kg ganaxolone.

(71) The method of any one of Specific Embodiments 55 to 59 comprising administering an intravenous infusion of the ganaxolone formulation to the patient, with or without an initial bolus dose.

(72) The method of Specific Embodiment 71 comprising administering the intravenous infusion for 1 to 10 consecutive days at a rate of 1 to 10 mg/kg/hr without an initial bolus dose.

(73) The method of Specific Embodiment 72 comprising administering an initial bolus dose of from about 1 mg/kg to about 20 mg/kg ganaxolone, followed within 24 hours by administration of an intravenous infusion of the ganaxolone formulation for 1 to 10 consecutive days at a rate of 1 to 10 mg/kg/hr.

(74) The method of Specific Embodiment 73, wherein the initial bolus dose provides a sufficient amount of ganaxolone to provide an initial plasma $C_{max}$ of ganaxolone of at least 1000 ng/mL in the patient and the concentration of ganaxolone in the patient's plasma does not fall below 25% of the initial $C_{max}$ until after the infusion is concluded.

(75) The method of Specific Embodiment 73, wherein the initial bolus dose provides a sufficient amount of ganaxolone to provide an initial plasma $C_{max}$ of ganaxolone of about 100 ng/mL to about 8000 ng/mL in the patient, the patient is then administered an intravenous infusion of the ganaxolone formulation at a constant dose sufficient to provide a concentration of ganaxolone in the patient's plasma of at least 40% of $C_{max}$, followed by an intravenous infusion of ganaxolone formulation at a gradually reducing dose so that the concentration of ganaxolone in the patient's plasma is less than 20% of $C_{max}$ when the intravenous infusion is concluded.

(76) The method any one of Specific Embodiments 55 to 75 wherein the ganaxolone formulation is a first active agent and is administered concurrently or sequentially with at least one additional active agent.

(77) The method of Specific Embodiment 76 wherein the at least one additional active agent is an anticonvulsant or anesthetic/sedative.

(78) The method of Specific Embodiment 77 wherein the at least one additional active agent is an anticonvulsant chosen from a GABAA receptor modulator, a sodium channel blocker, a GAT-1 GABA transporter modulator, a GABA transaminase modulator, a voltage-gated calcium channel blocker, and a peroxisome proliferator-activated alpha modulator.

(79) The method of Specific Embodiment 77 wherein the at least one additional active agent is an anesthetic/sedative chosen from an inhalational anesthetics (including desflurane, enflurane, ethyl chloride, halothane, isoflurane, methoxyflurane, sevoflurane, and trichloroethylene), an intravenous, non-barbiturate anesthetics (including atracurium, cisatracurium, etodimidate, ketamine, propofol, and rocuronium), a barbiturate anesthetic (including amobarbital, methohexital, pentobarbital, phenobarbital, secobarbital, thiamylal, and thiopental), and a benzodiazepine anesthetic (including diazepam, flunitrazepam, lorazepam, and midazolam).

(80) The method of Specific Embodiment 79, wherein the additional active agent is an anesthetic/sedative and the patient is given a sufficient dosage of the anesthetic/sedative to induce coma.

(81) The method of Specific Embodiment 80, wherein the additional active agent is a barbiturate.

(82) The method of Specific Embodiment 81, wherein the additional active agent is pentobarbital or thiopental.

(83) The method of Specific Embodiment 79, wherein the additional active agent is propofol.

(84) The method of Specific Embodiment 76, wherein a first additional active agent is an anticonvulsant and a second additional active agent is an anesthetic/sedative.

(85) The method of Specific Embodiment 84, wherein the anticonvulsant is carbamazepine, tiagabine, levetiracetam, lamotrigine, pregabalin, gabapentin, or phenytoin and the anesthetic/sedative is pentobarbital, thiopental, or propofol.

EXAMPLES

ABBREVIATIONS

ALLO Allopregnanolone
GNX Ganaxolone
HES Hydroxy ethyl starch

Example 1. Preparation of Ganaxolone Nanosuspension (10% wt) Via Wet Bead Milling An aqueous slurry (250 g) containing ganaxolone (25 g), hydroxyethyl starch (7.5 g), sodium deoxycholate (0.5 g) and 30% simethicone (1 drop) was milled using a Netzsch Mill (Minicer) with 0.3 mm YTZ beads (Yttrium stabilized grinding media, Tosoh Corporation, Japan, $ZrO_2+HfO_2$ (95 wt % (weight %)), $Y_2O_2$ (5 wt %)). Two additional portions of solid sodium deoxycholate (0.5 g each) were added at 100 and 130 min after milling had started. The particle size of the milled slurry was measured using a Horiba LA-910 laser diffraction particle size analyzer. After 170 minutes of milling, D50 was 192 nm (188 nm after 1 min sonication). At this point, milling was stopped and the milled slurry was kept at room temperature overnight. The next morning, milling was resumed until the total milling time had reached 320 minutes, at which point D50 was 167 nm (169 nm after 1 min sonication). The D50 particle size was measured on a Horiba 910 Laser Light Scattering instrument.

Example 2. Preparation of Ganaxolone Nanosuspension (20% wt) Via Wet Bead Milling An aqueous slurry (250 g) containing ganaxolone (50 g), hydroxyethyl starch (15 g), sodium deoxycholate (3 g) and 30% simethicone (0.15 g) was milled using a Netzsch mill (Minicer) with 0.3 mm YTZ beads for 240 minutes. The D50 of the milled slurry was 189 nm (185 nm after 1 min sonication).

Example 3. Preparation of Ganaxolone Nanosuspension (20% wt) Via Wet Bead Milling Using 0.2 mm YTZ Beads An aqueous ganaxolone slurry having the same composition as described in Example 2 was milled using a Netzsch mill (Minicer) with 0.2 mm YTZ beads for 245 minutes. The D50 was 172 nm (167 nm after 1 minute sonication).

Example 4. Preparation of Ganaxolone Nanosuspension Containing Dextran 70 Via Wet Bead Milling An aqueous ganaxolone slurry (250 g) containing ganaxolone (25 g), dextran 70 (7.5 g), sodium deoxycholate (1.5 g), and 30% simethicone (0.075 g) was milled using a Netzsch mill (Minicer) with 0.2 mm YTZ beads for 195 minutes to obtain a ganaxolone nanosuspension with D50 of 159 nm (158 nm after 1 minute sonication). Prolonged milling caused particle size to increase to 215 nm (212 nm after 1 min sonication).

Example 5. Preparation of Ganaxolone Nanosuspension Containing 10% Hydroxyethyl Starch An aqueous ganaxolone suspension (250 g) containing ganaxolone (25 g), hydroxyethyl starch (25 g), sodium deoxycholate (3 g) and 30% simethicone (0.15 g) was milled using a Netzsch mill (Minicer) with 0.2 mm YTZ beads for 150 minutes to obtain a ganaxolone nanosuspension with D50 value of 139 nm (140 nm after 1 minute sonication).

Example 6. Dilution of Ganaxolone Nanosuspension Concentrate and Sterile Filtration Through 0.2 Micron Filter The ganaxolone nanosuspension of Example 5 was diluted 5-fold with HPLC grade water to obtain a nanosuspension containing about 20 mg/mL ganaxolone. This suspension was filtered through a 0.2 um syringe filter (Cellulose acetate, 25 mm, 0.2 µm, product #: 13-250020-25 PK, Scientific Strategies). The particle size of the filtered ganaxolone suspension was measured and found to be: D50, 143 nm (143 nm after 1 minute sonication); D90, 219 nm; D95, 289 nm.

Example 7. Procedure for Freeze Drying Ganaxolone Nanosuspension

Ganaxolone nanosuspension, prepared according to the procedure of Examples 1-5 (2 mL), was placed in a 20 mL HDPE scintillation vial followed by addition of appropriate amount of solid inactive pharmaceutical excipients. After the solid excipients were dissolved by visual inspection, the vial was immersed in a dry ice acetone bath until the content in the vial was completely frozen. Solid excipients include, for example, sucrose, mannitol, dextrose, lactose, D-sorbitol, and NaCl.

The vial was then placed in a freeze dryer flask for lyophilization and lyophilized until a dry solid was obtained. The lyophilized powder was re-dispersed in either water or 0.9% saline prior to particle size measurement. Table 1 shows lyophilized ganaxolone formulations containing hydroxyethyl starch (ganaxolone/hydroxyethyl starch=3.3:1). The D50 values of the Table 1 formulations prior to freeze drying were between 214-230 nm. Table 2 shows lyophilized ganaxolone formulations containing dextran 70 (ganaxolone/dextran 70=3.3:1). The D50 value prior to freeze-drying of the ganaxolone nanosuspension with sucrose was 0.212 µm (microns) prior to freeze drying. Table 3 shows lyophilized ganaxolone formulations containing hydroxyethyl starch (ganaxolone/hydroxyethyl starch=1:1). The D50 value prior to freeze drying was 0.139 µm.

TABLE 1

Particle size values (D50) of freeze dried ganaxolone nanosuspension formulations (ganaxolone to hydroxyethyl starch 130/0.4 ratio is 3.3:1) after redispersion in water

| Formulation | Composition (wt %) | | | | | | |
| --- | --- | --- | --- | --- | --- | --- | --- |
| | A | B | C | D | E | F | G |
| Ganaxolone | 73.48 | 53.74 | 42.36 | 53.74 | 42.36 | 53.74 | 42.36 |
| Hydroxyethyl starch | 22.04 | 16.12 | 12.71 | 16.12 | 12.71 | 16.12 | 12.71 |
| Sodium deoxycholate | 4.41 | 3.22 | 2.54 | 3.22 | 2.54 | 3.22 | 2.54 |
| Simethicone (30%) | 0.07 | 0.05 | 0.04 | 0.05 | 0.04 | 0.05 | 0.04 |
| Sucrose | 0.00 | 26.87 | 42.36 | 0.00 | 0.00 | 0.00 | 0.00 |
| Mannitol | 0.00 | 0.00 | 0.00 | 26.87 | 42.36 | 0.00 | 0.00 |
| dextrose | 0.00 | 0.00 | 0.00 | 0.00 | 0.00 | 26.87 | 42.36 |
| lactose | 0.00 | 0.00 | 0.00 | 0.00 | 0.00 | 0.00 | 0.00 |
| D-Sorbitol | 0.00 | 0.00 | 0.00 | 0.00 | 0.00 | 0.00 | 0.00 |
| NaCl | 0.00 | 0.00 | 0.00 | 0.00 | 0.00 | 0.00 | 0.00 |
| Total | 100.00 | 100.00 | 100.00 | 100.00 | 100.00 | 100.00 | 100.00 |
| D50 (µm)[a] | 24.168 (3.518) | 0.320 (0.225) | 0.279 (0.209) | 51.85 (6.510) | 20.48 (3.36) | 0.330 (0.252) | 11.223 (4.688) |

| Formulation | Composition (wt %) | | | | | |
| --- | --- | --- | --- | --- | --- | --- |
| | H | I | J | K | L | M |
| Ganaxolone | 53.74 | 42.36 | 53.74 | 42.36 | 40.64 | 29.75 |
| Hydroxyethyl starch | 16.12 | 12.71 | 16.12 | 12.71 | 12.19 | 8.93 |

TABLE 1-continued

Particle size values (D50) of freeze dried ganaxolone nanosuspension formulations (ganaxolone to hydroxyethyl starch 130/0.4 ratio is 3.3:1) after redispersion in water

| | | | | | | |
|---|---|---|---|---|---|---|
| Sodium deoxycholate | 3.22 | 2.54 | 3.22 | 2.54 | 2.44 | 1.79 |
| Simethicone (30%) | 0.05 | 0.04 | 0.05 | 0.04 | 0.04 | 0.03 |
| Sucrose | 0.00 | 0.00 | 0.00 | 0.00 | 40.64 | 59.51 |
| Mannitol | 0.00 | 0.00 | 0.00 | 0.00 | 0.00 | 0.00 |
| dextrose | 0.00 | 0.00 | 0.00 | 0.00 | 0.00 | 0.00 |
| lactose | 26.87 | 42.36 | 0.00 | 0.00 | 0.00 | 0.00 |
| D-Sorbitol | 0.00 | 0.00 | 26.87 | 42.36 | 0.00 | 0.00 |
| NaCl | 0.00 | 0.00 | 0.00 | 0.00 | 4.06 | 0.00 |
| Total | 100.00 | 100.00 | 100.00 | 100.00 | 100.00 | 100.00 |
| D50 (μm)$^a$ | 0.352 (0.245) | 0.971 (0.418) | 0.328 (0.216) | 0.335 (0.227) | 0.226 (0.199) | 0.207 (0.208) |

$^a$D50 values in parenthesis are after 1 minute sonication.

TABLE 2

Particle size values (D50) of freeze dried ganaxolone nanosuspension formulations containing dextran 70 after redispersion in water

| | Composition (wt %) | |
|---|---|---|
| Formulation | A (no sucrose) | B (with sucrose) |
| Ganaxolone | 73.48 | 18.65 |
| Dextran 70 | 22.04 | 5.60 |
| Sodium deoxycholate | 4.41 | 1.12 |
| 30% Simethicone emulsion | 0.07 | 0.02 |
| Sucrose | 0.00 | 74.61 |
| Total | 100.00 | 100.00 |
| D50 (μm)$^a$ | 26.165 (3.793) | 0.224 (0.224) |

$^a$D50 values in parenthesis are after 1 minute sonication.

TABLE 3

Particle size values (D50) of freeze dried ganaxolone nanosuspension formulations (ganaxolone to hydroxyethyl starch 130/0.4 ratio is 1:1) after redispersion in 0.9% saline for injection

| | Composition (wt %) | |
|---|---|---|
| Formulation | A (no sucrose) | B (with sucrose) |
| Ganaxolone | 47.13 | 24.26 |
| hydroxyethyl starch | 47.13 | 24.26 |
| Sodium deoxycholate | 5.66 | 2.91 |
| 30% Simethicone emulsion | 0.08 | 0.04 |
| Sucrose | 0.00 | 48.52 |
| Total | 100.00 | 100.00 |
| D50 (μm)$^a$ | 0.275 (0.174) | 0.161 (0.150) |

$^a$D50 values in parenthesis are after 1 minute sonication.

Example 8. Particle Size Storage Stability of Ganaxolone Nanosuspension Containing 20% Ganaxolone, 6% Hydroxyethyl Starch, 1.2% Sodium Deoxycholate and 0.06% Simethicone (30% Emulsion)

A ganaxolone nanosuspension containing (wt %) 20% ganaxolone, 6% hydroxyethyl starch, 1.2% sodium deoxycholate, and 0.6% simethicone (30% emulsion) was prepared by the procedure described in Example 2. The D50 particle size was measured on a Horiba 910 Laser Light Scattering instrument over a 17 day period. Initial particle size was approximately 189 nm. Particle size initially increased about 10% but remained stable after the initial increase from the remainder of the 17 day period. See FIG. 1.

Example 9. Ganaxolone Nanosuspension Containing Poloxamer 188

A KDL Bachofen Mill was configured with the batch chamber attachment (approx. 350 ml) and the 96 mm polyurethane rotor attached to the shaft. Next, 265 ml of 0.3 mm yttria-zirconia beads were added dry to the chamber, followed by 176.7 gm of the Ganaxolone (GNX) slurry. Slowly, over 15 minutes, the ganaxolone slurry was added to the milling media containing Pluronic F-68 (Poloxamer 188) with sustained stirring. The mixture was stirred slowly overnight. The slurry was milled at Speed 1 (1500 rpm) with intermittent measurement of particle size. After 90 min, the D50 particle size was determined to be 378 nm. The D50 measurement was measured on a Horiba 910 Laser Light Scattering instrument.

| Milling Media | |
|---|---|
| Pluronic F-68 | 27.0 g |
| Sodium deoxycholate | 2.7 g |
| Simethicone emulsion 30% | 0.2 g |
| Water (DI) | to 200 g |
| Ganaxolone Slurry | |
| Ganaxolone | 50 g |
| Milling Media | 150 g |
| Final Milling Composition (wt %) | |
| Ganaxolone | 25% |
| Pluronic F-68 | 10% |
| Deoxycholate | 1% |

Example 10. Ganaxolone Nanosuspension Containing Poloxamer 188, 0.1 mm Beads The KDL Bachofen mill was configured with the batch chamber attachment (approx. 350 ml) and the 96 mm polyurethane rotor attached to the shaft. Next, 300 ml of 0.1 mm yttria-zirconia beads were added dry to the chamber, followed by 134.6 gm Ganaxolone (GNX) slurry having the composition given in preceding Example 9. The slurry was milled for 60 minutes and the D50 particle size was measured after 20, 40, 60 minutes of milling.

| Time (min) | Particle size, μm | After sonication, μm |
|---|---|---|
| 20 | 0.182 | 0.183 |
| 40 | 0.164 | 0.165 |
| 60 | 0.162 | |

Example 11. Ganaxolone Nanosuspension Containing 12.5% Poloxamer 188 and Dextran The KDL Bachofen mill was configured with the batch chamber attachment (approx. 350 ml) and the 96 mm polyurethane rotor attached to the shaft. Next, 300 ml of 0.1 mm yttria-zirconia beads were added dry to the chamber, followed by 176.5 gm of the Ganaxolone (GNX) milling suspension. The ganaxolone milling suspension was prepared by combining the dextran, Pluronic F-68, sodium deoxycholate, and simethicone emulsion ingredients with stirring, and then adding the ganaxolone last with stirring. The suspension stirred for 1.5 hr. The suspension (176.5 gm was added to the batch chamber and the mill started at Speed setting 1. The slurry was milled for 60 minutes and the D50 particle size was measured after 20, 40, 50, and 60 minutes of milling.

| Ganaxolone Milling Suspension | |
|---|---|
| Dextran (40K mol. wt.) | 10.0 g |
| Pluronic F-68 | 25.0 g |
| Sodium deoxycholate | 0.5 g |
| Simethicone emulsion 30% | 0.2 g |
| Ganaxolone | 20.0 g |
| Water (DI) | to 200 g |
| Final Milling Composition (wt %) | |
| Ganaxolone | 20% |
| Dextran | 5% |
| Pluronic F-68 | 25% |
| Sodium Deoxycholate | 0.25% |

| Time (min) | Particle size, μm | After sonication, μm |
|---|---|---|
| 20 | 0.221 | 0.219 |
| 40 | 0.173 | — |
| 50 | 0.166 | 0.168 |
| 60 | 0.164 | — |

Figure 2:
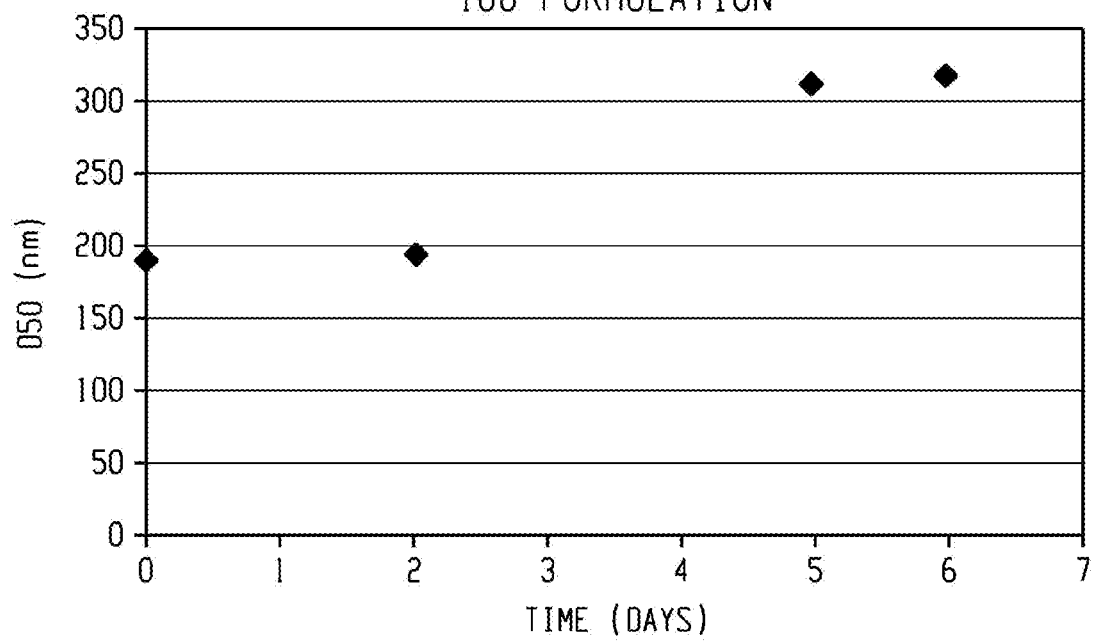
FIG. 2. D50 values of a ganaxolone nanosuspension stabilized by poloxamer 188 and sodium deoxycholate monitored over a 6-day period. The nanosuspension contained ganaxolone (10%), poloxamer 188 (12.5%), dextran (40K MW) (5%), sodium deoxycholate (0.25%).

The milled suspension above (64.4 gm) was treated with methyl paraben Na (0.074 gm and citric acid (0.027 gm) and the particle size monitored over time. The results are presented graphically in FIG. 2.

| Day | Particle size, μm |
|---|---|
| 0 | 0.191 |
| 2 | 0.194 |
| 5 | 0.313 |
| 6 | 0.317 |

Example 12. Preparation of Allopregnanolone Nanosuspension Via Wet Bead Milling An aqueous slurry (125 g) containing allopregnanolone (12.5 g), hydroxyethyl starch (12.5 g), sodium deoxycholate (1.5 g) and 30% simethicone emulsion (0.075 g) was milled using a Netzsch mill (Minicer) with 0.2 mm YTZ beads for 210 minutes. The D50 of the milled slurry was 96 nm (96 nm after 1 min sonication). Particle size distribution plots for ganaxolone and allopregnanolone formulations prepared as described in Examples 12-15 are provided in FIG. 6.

Example 13. Preparation of Allopregnanolone Nanosuspension Via Wet Bead Milling An aqueous slurry (169.7 g) containing allopregnanolone (21.5 g), hydroxyethyl starch 130/0.4 (26.5 g), sodium deoxycholate (2.1 g) and 30% simethicone emulsion (0.10 g) was milled using a Netzsch mill (Minicer) with 0.2 mm YTZ beads for 240 minutes. The D50 of the milled slurry was 98 nm (97 nm after 1 min sonication).

Example 14. Preparation of Ganaxolone Nanosuspension Containing Povidone Via Wet Bead Milling An aqueous ganaxolone slurry (175 g) containing ganaxolone (17.5 g), povidone (17.5 g), sodium deoxycholate (2.1 g), and 30% simethicone (0.105 g) was milled using a Netzsch mill (Minicer) with 0.2 mm YTZ beads for 180 minutes to obtain a ganaxolone nanosuspension with D50 of 109 nm (111 nm after 1 minute sonication). The D50 value was 114 nm (113 nm after 1 minute sonication) after 3 days of storage at ambient conditions.

Example 15. Preparation of Ganaxolone Nanosuspension Containing Hydroxyethyl Starch Via Wet Bead Milling An aqueous ganaxolone slurry (175 g) containing ganaxolone (17.5 g), hydroxyethyl starch 130/0.4 (17.5 g), sodium deoxycholate (2.1 g), and 30% simethicone (0.105 g) was milled using a Netzsch mill (Minicer) with 0.2 mm YTZ beads for 240 minutes to obtain a ganaxolone nanosuspension with D50 of 106 nm (107 nm after 1 minute sonication).

Example 16. Bioavailability of Nanosuspension and Captisol Formulations

The ganaxolone concentration in rat plasma and rat brain following administration of 9, 12, or 15 mg/kg ganaxolone as a Captisol solution or hydroxyethyl starch 130/0.4 nanosuspension was determined. Male Sprague-Dawley rats, 8-9 weeks of age, from Harlan Labs were used. Animals received food and water ad libitum throughout the study and were maintained on a 12 hr/12 hr light dark schedule with lights on at 7:00 AM. Animals were weighed prior to compound administration. Ganaxolone solutions were formulated at 2.5 mg/mL and the volume was adjusted to accommodate larger dosages. Injections were administered via the tail vein as a bolus dose.

Plasma was collected and 5, 15, 30, 60 or 120 minutes post dosing. Brains were collected at 5, 30, and 120 minutes post dosing. Three rats were used for each time point, and the reported ganaxolone levels are the mean of ganaxolone plasma or brain levels of all three rats. Blood was collected by retro-orbital bleed or cardiac puncture. Blood samples were collected into $K^{2+}$EDTA coated tubes. Plasma samples were prepared by spinning blood in a refrigerated centrifuge (3000 rpm for 10 min at 4° C.). Plasma PK characteristics were similar for the ganaxolone Captisol and nanosuspension formulations (see FIG. 3), however the nanosuspension produced significantly higher and longer lasting brain ganaxolone levels (See FIG. 4). The ganaxolone Captisol and nanosuspension formulations used in this experiment and the experiment presented in the next example are provided in TABLE 4A.

TABLE 4A

| Formulation | Composition (wt %) | Ganaxolone Concentration (mg/mL) |
| --- | --- | --- |
| Ganaxolone/Captisol solution | Ganaxolone: 0.22%<br>Captisol: 26.84%<br>Water: 72.94% | 2.5 mg/mL |
| Ganaxolone Nanosuspension | Ganaxolone: 0.25%<br>Hydroxyethyl Starch 130/0.4: 0.25%<br>Sodium Deoxycholate: 0.03%<br>Simethicone, 30% emulsion: 0.0006%<br>Water: 99.47% | 2.5 mg/mL |

Figure 5A:
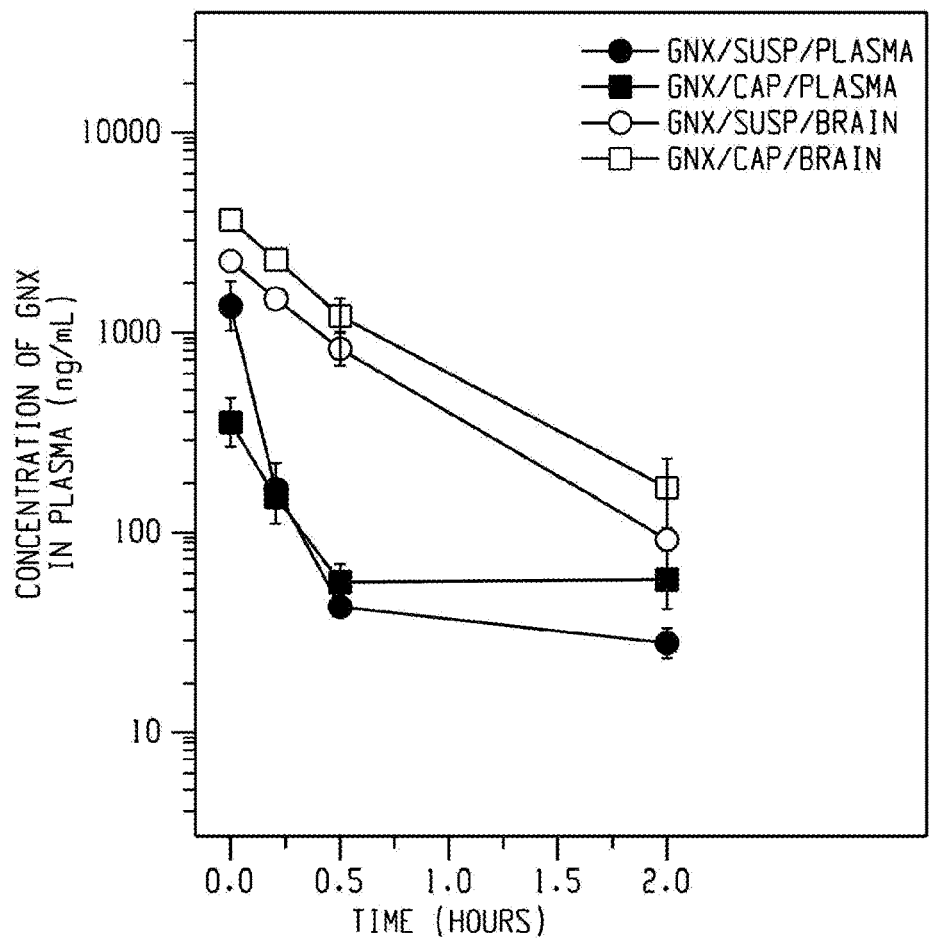
FIG. 5A depicts Ganaxolone brain and plasma levels in rats receiving intravenous Ganaxolone as a Captisol solution or a nanosuspension.
Figure 5B:
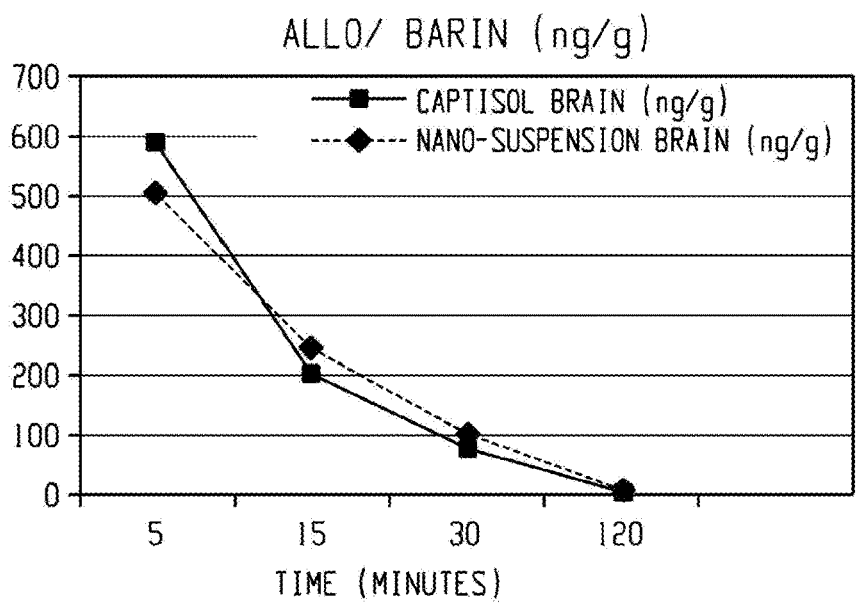
FIG. 5B depicts Allopregnanolone brain levels, in rats. Experiment performed as for Ganaxolone.
Figure 6A:
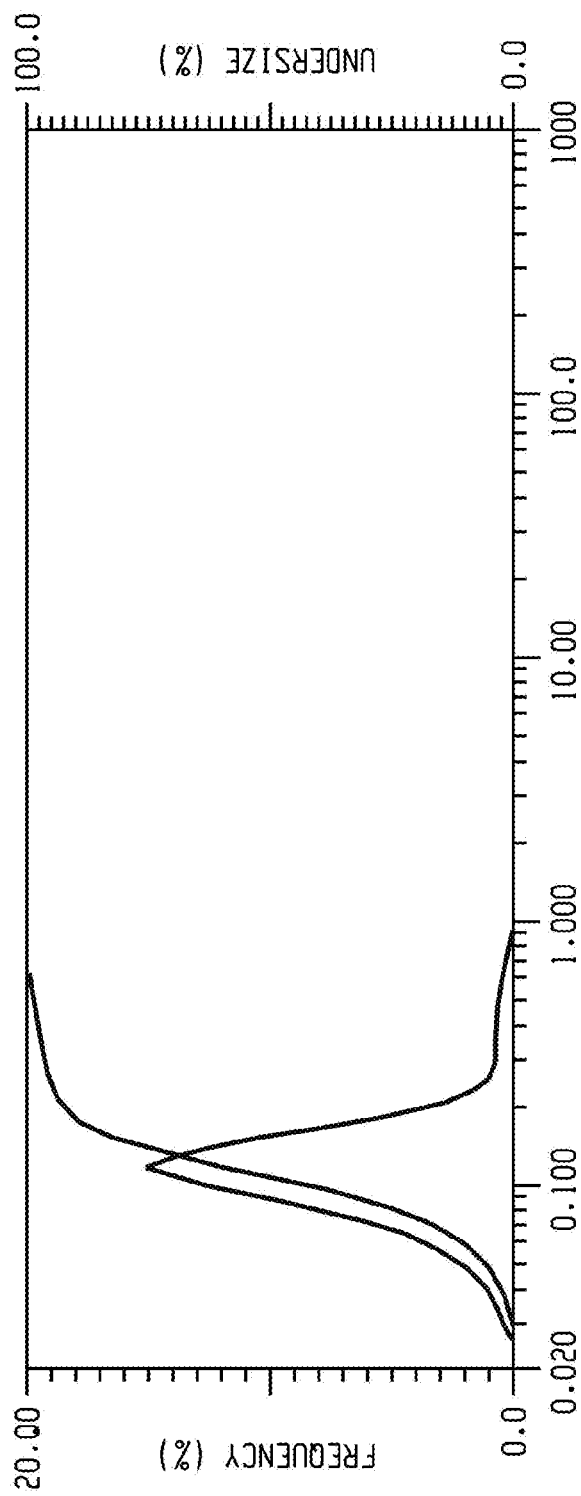
FIG. 6A depicts Particle size distribution curves for particles containing ganaxolone and hydroxyethyl starch (D50=106 nm).
Figure 6B:
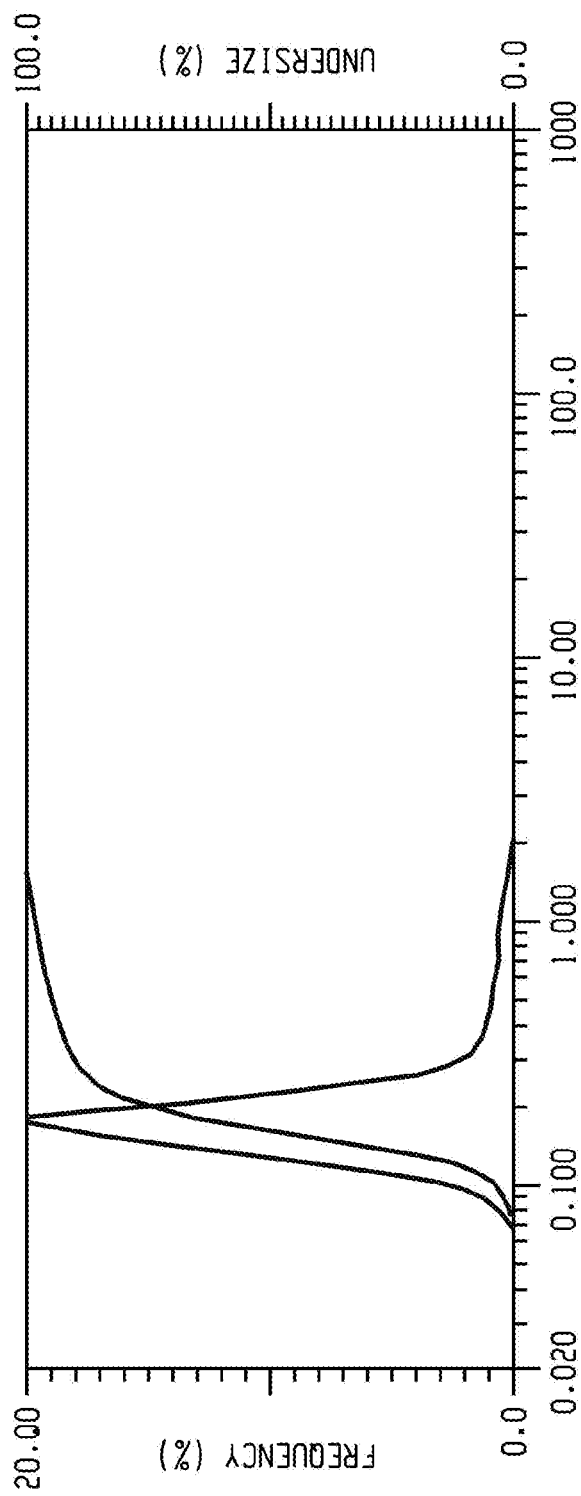
FIG. 6B depicts Particle size distribution curves for particles containing ganaxolone and Dextran 70 (D50=111 nm).
Figure 6C:
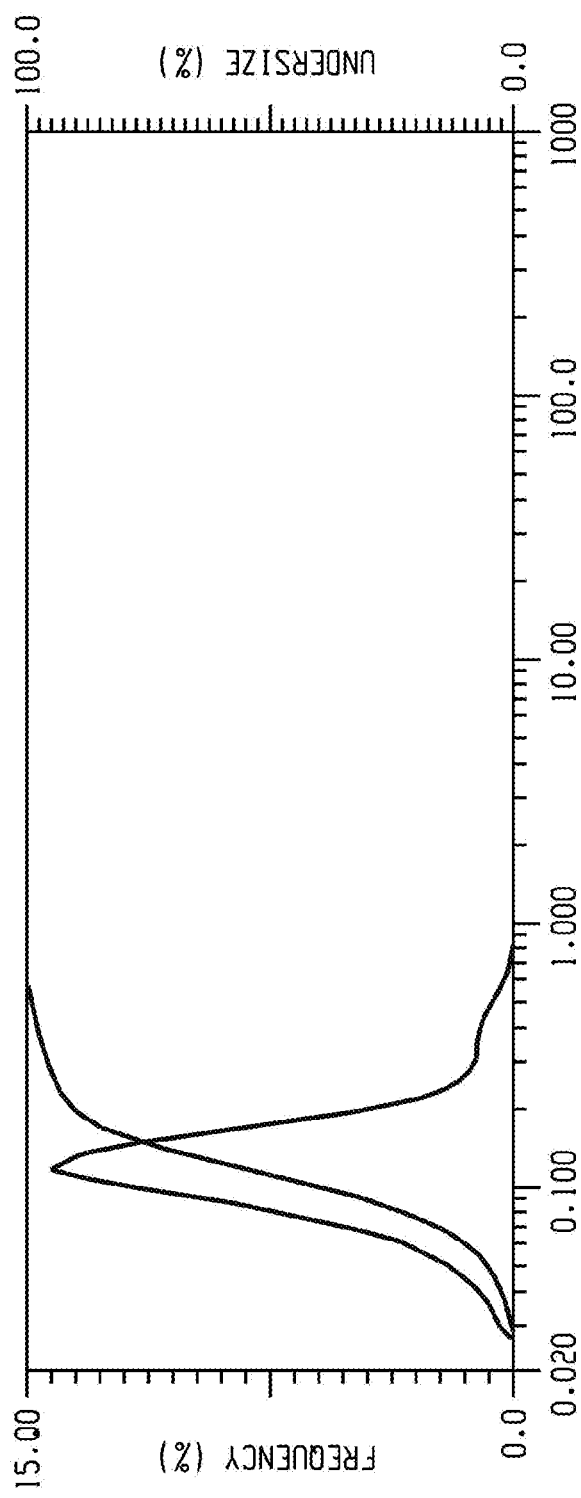
FIG. 6C depicts Particle size distribution curves for particles containing ganaxolone and povidone (D50=109 nm)
Figure 6D:
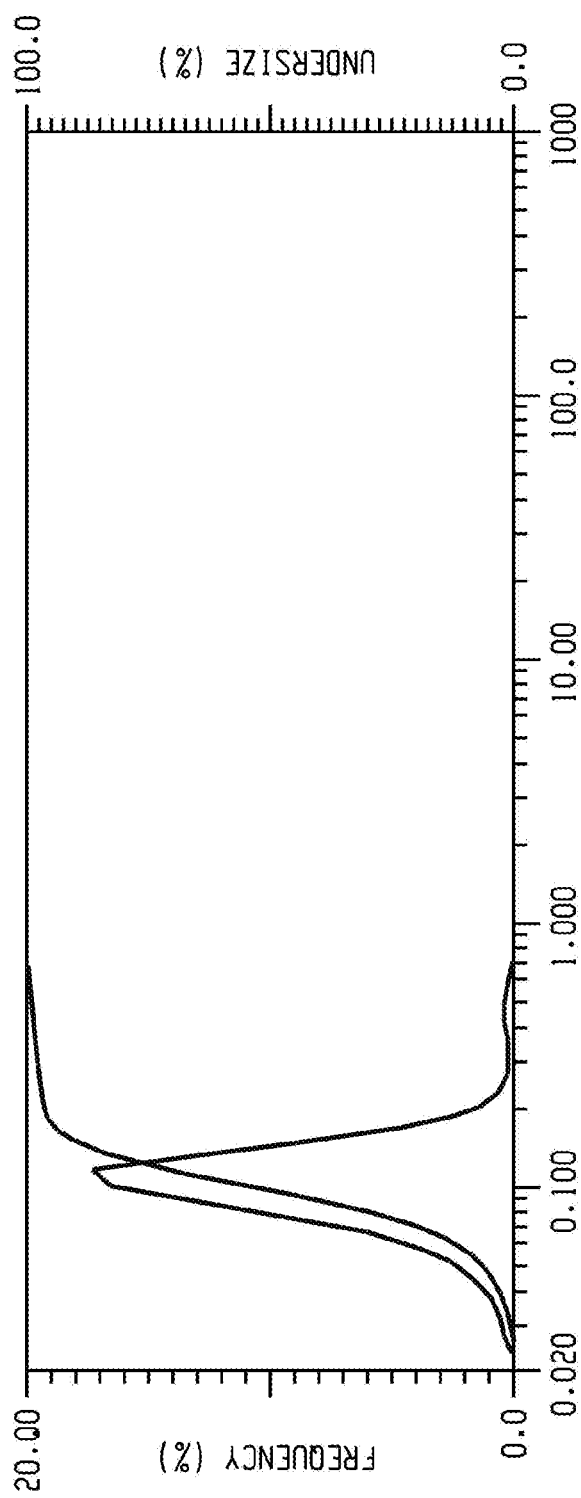
FIG. 6D depicts Particle size distribution curves for particles containing allopregnanolone and hydroxyethyl starch (D50=96 nm).

Example 17. Brain and Plasma Levels of Ganaxolone and Allopregnanolone Nanosuspension and Captisol Solutions Rats were dosed with approximately 1 mg/ml ganaxolone as a nanosuspension or as a Captisol solution. A dosage of 1 mg/kg was used. The ganaxolone plasma levels and brain levels were determined at 5, 15, 30, and 120 minutes. Three rats were used for each time point, and the reported ganaxolone levels are the mean of ganaxolone plasma or brain levels of all three rats. The same study was conducted using allopregnanolone, as a nanosuspension or Captisol solution. The ganaxolone and allopregnanolone formulations used in this experiment are given in TABLE 4B. The results of this experiment are shown in FIG. 5.

TABLE 4B

| Formulation | Composition (wt %) | Drug Concentration (mg/mL) |
| --- | --- | --- |
| Ganaxolone/Captisol solution | Ganaxolone: 0.097%<br>Captisol: 5.85%<br>Water: 94.05% | 0.99 mg/ml |
| Ganaxolone Nanosuspension (D50: 143 nm) | Ganaxolone: 0.10%<br>Hydroxyethyl Starch 130/0.4: 0.10%<br>Sodium Deoxycholate: 0.012%<br>Simethicone, 30% emulsion: 0.0006%<br>Water: 99.79% | 0.98 mg/mL |
| Allopregnanolone/ Captisol solution | Ganaxolone: 0.079%<br>Captisol: 5.85%<br>Water: 94.07% | 0.81 mg/mL |
| Allopregnanolone nanosuspension (D50: 95 nm) | Allopregnanolone: 0.10%<br>Hydroxyethyl Starch 130/0.4: 0.10%<br>Sodium Deoxycholate: 0.012%<br>Simethicone, 30% emulsion: 0.0006%<br>Water: 99.79% | 0.95 mg/mL |

Example 18. Behavioral Observations and Sedation Levels of Ganaxolone Nanosuspension and Captisol Solutions This study consisted of administering ganaxolone at 9, 12, or 15 mg/mL or vehicle (negative control) in the Captisol and nanosuspension formulations. Injections were administered via the tail vein as a bolus dose. The behavior of the animals was recorded at 5, 15, 30, 60, 120, 180, and 240 minutes post dosing. Terminal blood/plasma and brain samples were collected at 4 hours.

Animals are as described in Example 16. Four animals were used for each treatment group. TABLE 5 below illustrates the experimental design for the sedation experiments. The formulations are described in Example 16, TABLE 4A. For each of the experimental conditions listed in TABLE 5 the evaluation and endpoint is (1) Sedation level and duration and (2) ganaxolone level in plasma and brain at experiment termination (4 hours after dosing).

TABLE 5

| Treatment | Formulation | Group Size | Dose (mg/kg) |
| --- | --- | --- | --- |
| Vehicle | 30% Captisol | 4 | 0 |
| Ganaxolone | 30% Captisol | 4 | 9 |
| Ganaxolone | 30% Captisol | 4 | 12 |
| Ganaxolone | 30% Captisol | 4 | 15 |
| Vehicle | Nanosuspension | 4 | 0 |
| Ganaxolone | Nanosuspension | 4 | 9 |
| Ganaxolone | Nanosuspension | 4 | 12 |
| Ganaxolone | Nanosuspension | 4 | 15 |

Rats were observed for behavioral changes at 5, 15, 30, 60, 120, 180, and 240 minutes post administration. The observer was blinded to treatment. Qualitative behavioral changes were scored as follows along with any relevant observations.

0=awake, absence of sedation; no change in observed locomotion or behavior

1=light sedation; impaired; slowed movement, unresponsive to some stimuli, intact righting reflex.

2=deep sedation; sedated; lying on side, loss of righting reflex (LRR)

3=anesthesia; loss of toe-pinch reflex.

The health of the animals was monitored, particularly body temperature. If animals were cold to the touch, core body temperature was monitored by rectal probe and recorded. However, a heating pad not needed to maintain body temperature. Animals that received a sedation behavior score of 2 were placed on a blue pad lying on top of the bedding to prevent choking and these animals were closely monitored. All atypical or abnormal behavior or health issues were documented.

The behavior was scored using a four point scale (0, 1, 2, or 3) and the categorical data was analyzed by non-parametric Kruskal-Wallis ANOVA at each individual time point using Prism GraphPad (version 6). Post-hoc analysis consisted of Dunn's multiple (all pairwise) comparison tests, with significance set at $P<0.05$. PK data was analyzed by two-way ANOVA.

Figure 7A:
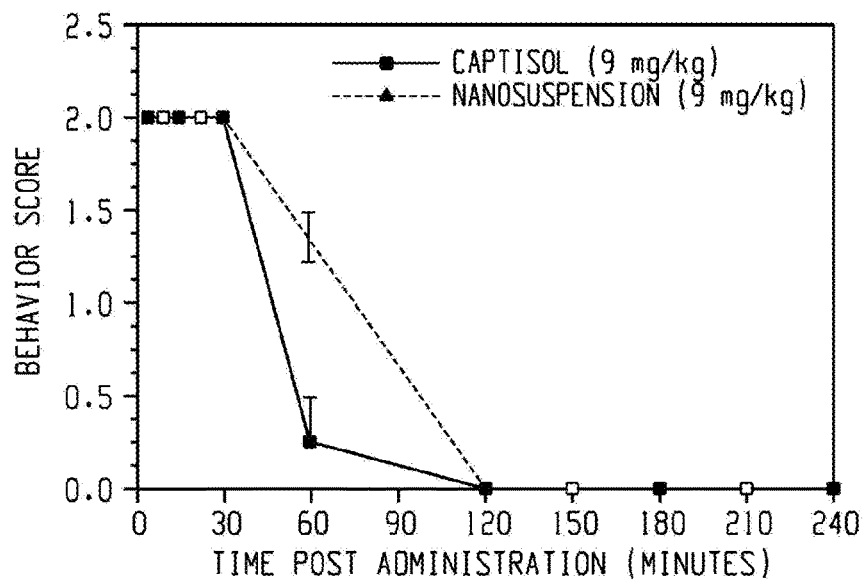
FIG. 7A depicts Behavior scores for 4 hours for ganaxolone nanoparticle hydroxyethyl starch formulation and positive control ganaxolone Captisol formulation in rats after a single intravenous injection for a dose of 9 mg/kg.
Figure 7B:
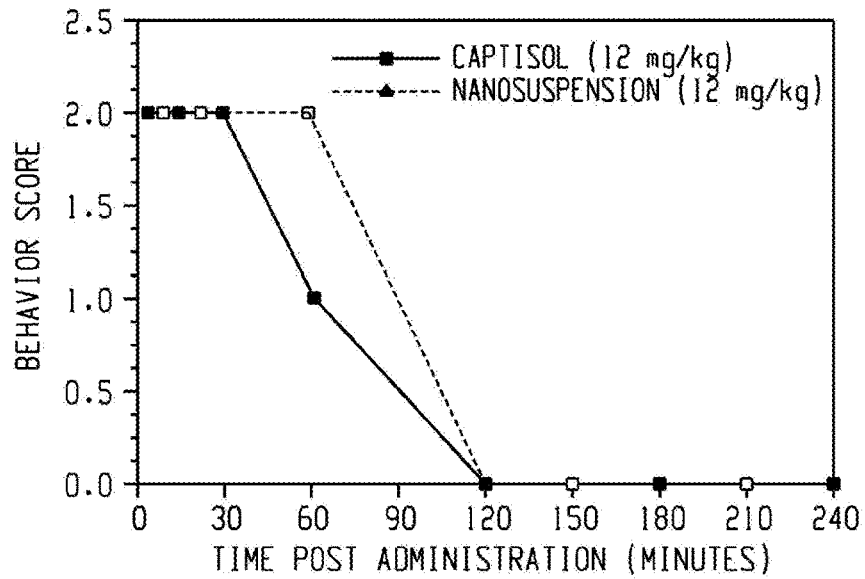
FIG. 7B depicts Behavior scores for 4 hours for ganaxolone nanoparticle hydroxyethyl starch formulation and positive control ganaxolone Captisol formulation in rats after a single intravenous injection for a dose of 12 mg/kg.
Figure 7C:
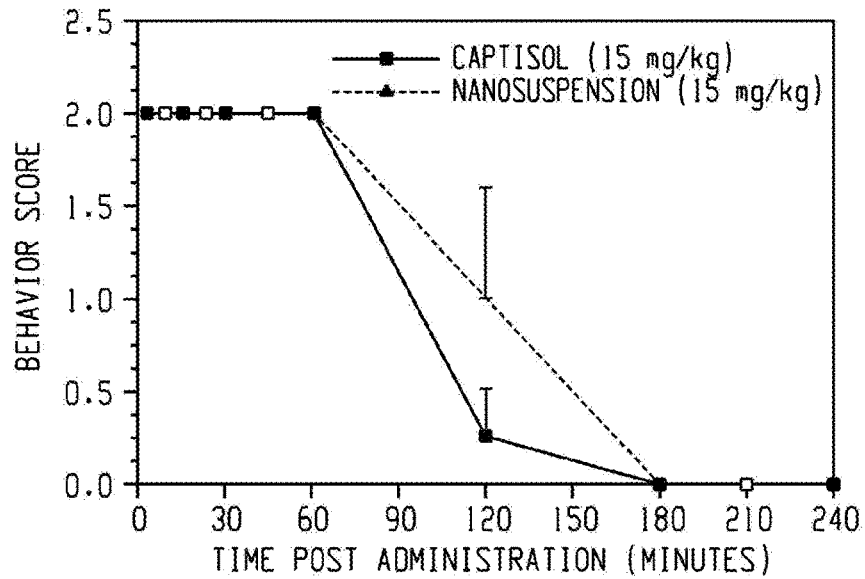
FIG. 7C depicts Behavior scores for 4 hours for ganaxolone nanoparticle hydroxyethyl starch formulation and positive control ganaxolone Captisol formulation in rats after a single intravenous injection for a dose of 15 mg/kg.

Both the Captisol and nanosuspension ganaxolone formulations were highly sedating and all rats at every dose-level received a sedation score of 2 at 5 min post injection (FIG. 7). The formulations exhibited dose-related effects on sedation as time progressed, with sedation lasting from 30-120 min, depending on dose and vehicle formulation (FIG. 7). The most sedating dose/formulation combination was the 15 mg/kg nanosuspension ganaxolone formulation; 2 of the 4 rats in this group were still sedated at 120 min following injection. All of the animals regardless of dose or formulation were awake 3 hours following injection.

In general, the nanosuspension formulation produced a longer duration of sedation than the Captisol formulation.

Individual Kruskal-Wallis non-parametric ANOVA's at each time point did not reveal any statistical differences between the Captisol and nanosuspension formulations. However, when analyzed by Mann-Whitney non-parametric t-test, the ganaxolone dose of 12 mg/kg in Captisol was significantly less sedating than the comparable nanosuspension ganaxolone dose at 60 min post administration.

The nanosuspension formulations were found to have increased behavioral effects as noted by: longer latency to wake-up, hemolysis/bloody urine (2 rats at 12 mg/kg and 1 rat at 15 mg/kg) and slowed/irregular breathing immediately following injection (1 rat at 12 mg/kg and 1 rat at 15 mg/kg).

Figure 3A:
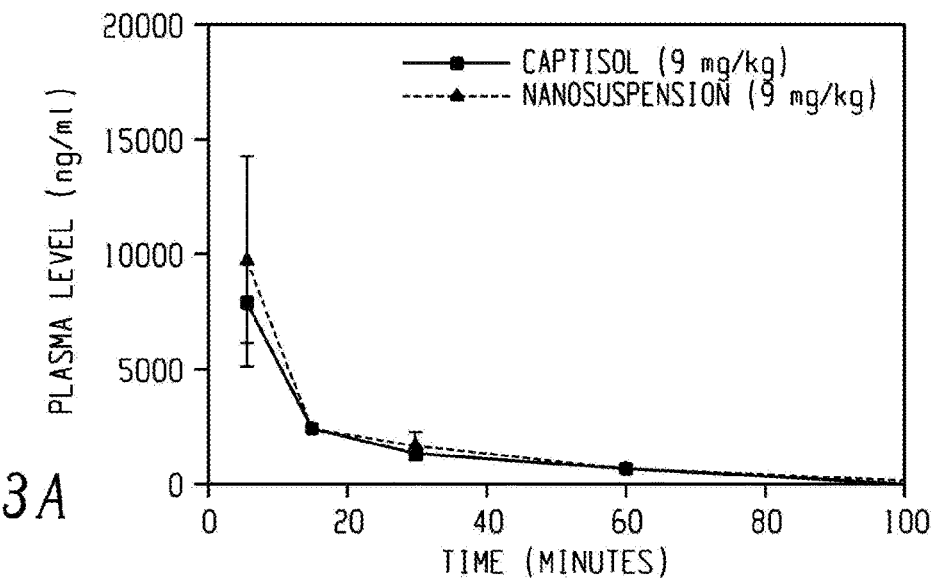
FIG. 3A depicts a Mean plasma ganaxolone concentration (ng/mL) for 2 hours for ganaxolone hydroxyethyl starch formulation and positive control ganaxolone Captisol formulation in rats after a single intravenous injection for a dose of 9 mg/kg.
Figure 3B:
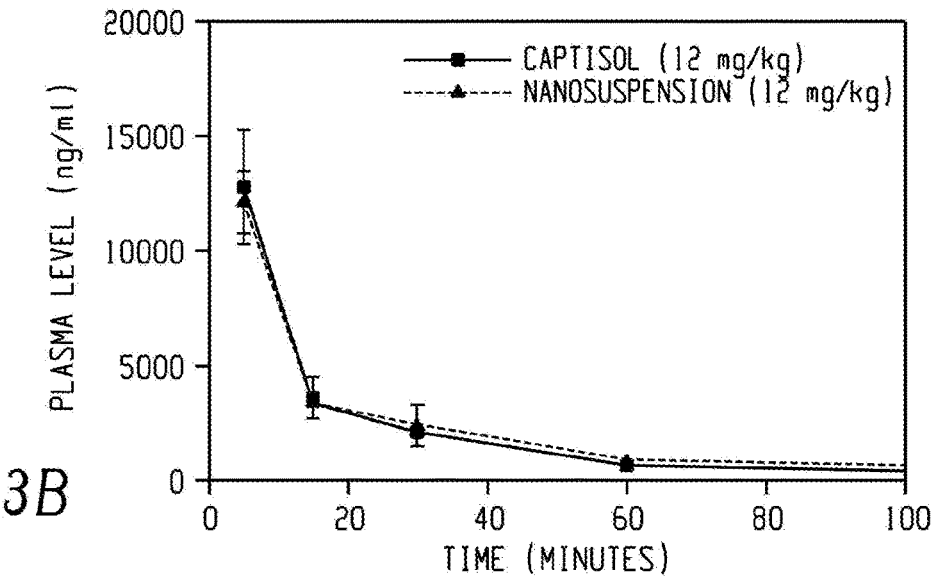
FIG. 3B depicts a Mean plasma ganaxolone concentration (ng/mL) for 2 hours for ganaxolone hydroxyethyl starch formulation and positive control ganaxolone Captisol formulation in rats after a single intravenous injection for a dose of 12 mg/kg.
Figure 3C:
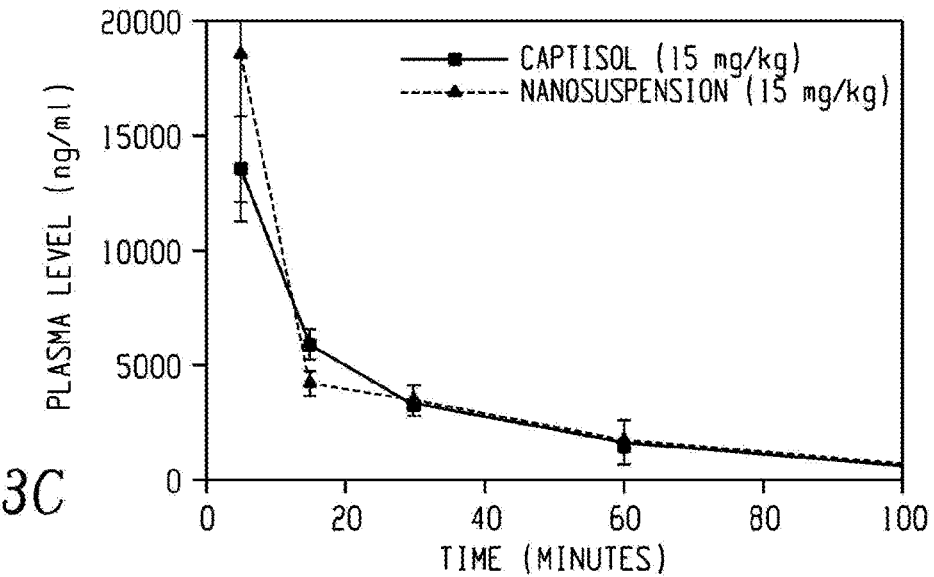
FIG. 3C depicts Mean plasma ganaxolone concentration (ng/mL) for 2 hours for ganaxolone hydroxyethyl starch formulation and positive control ganaxolone Captisol formulation in rats after a single intravenous injection for a dose of 15 mg/kg.
Figure 4A:
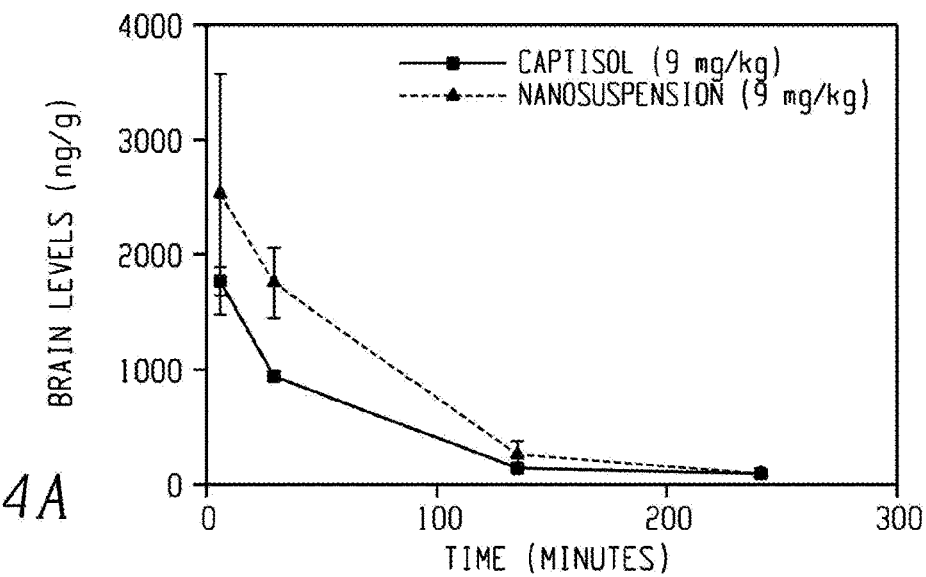
FIG. 4A depicts a Mean brain ganaxolone concentration (ng/mL). for 2 hours for ganaxolone hydroxyethyl starch formulation and positive control ganaxolone Captisol formulation in rats after a single intravenous injection for a dose of 9 mg/kg.
Figure 4B:
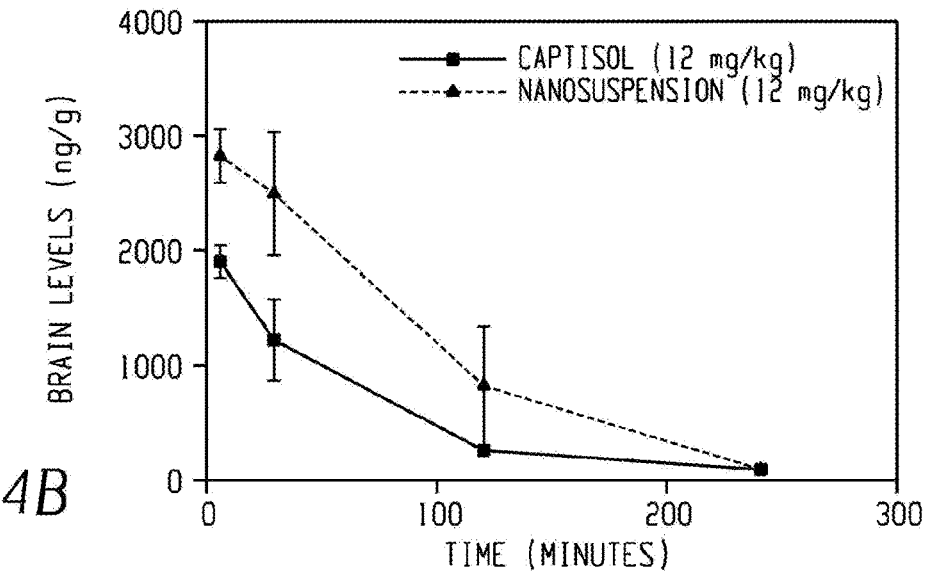
FIG. 4B depicts a Mean brain ganaxolone concentration (ng/mL). for 2 hours for ganaxolone hydroxyethyl starch formulation and positive control ganaxolone Captisol formulation in rats after a single intravenous injection for a dose of 12 mg/kg.
Figure 4C:
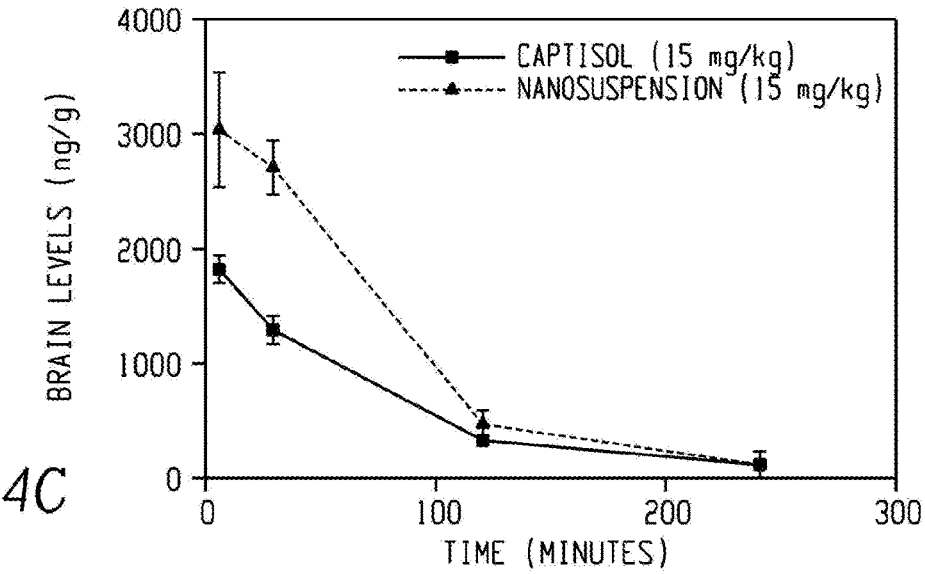
FIG. 4C depicts a Mean brain ganaxolone concentration (ng/mL). for 2 hours for ganaxolone hydroxyethyl starch formulation and positive control ganaxolone Captisol formulation in rats after a single intravenous injection for a dose of 15 mg/kg.

Plasma PK characteristics were similar between the two formulations. However, when examining brain levels the nanosuspension formulation produced significantly higher and longer lasting levels than the Captisol formulation. This brain PK paralleled the behavioral sedative response. These data are shown in FIGS. 3 and 4.

In summary, both the Captisol and nanosuspension formulations were highly sedating and exhibited dose-related effects on sedation as a function of time. The nanosuspensions appeared to have increased sedation. This increased behavioral response was most likely produced by higher neurosteroid brain absorption of the nanosuspension formulation.

Example 19. Ebeam Irradiation of Injectible Nanoparticle Formulations

Injectable neurosteroid nanoparticle formulations, prepared as described in the preceding examples were filled into 8 ml glass vials and capped. The vials were subjected to a 25 kGy dose of ebeam irradiation, a standard dose for producing sterile product. The nanoparticle formulations were assessed for appearance before and after ebeam irradiation, HPLC assay and impurity profiles before and after irradiation, relative viscosity before and after irradiation, and particle size (D50 and D90) before and after ebeam irradiation, No change in appearance was observed after ebeam irradiation for any of the neurosteroid nanosuspension tested. Neurosteroid assay and impurity profiles were determined via standard HPLC procedures. Viscosity measurements were obtained using an Ostwald viscometer. Relative viscosity was calculated as an efflux time ratio between nanosuspension and deionized water. D50 and D90 particle size measurements obtained using a Horiba 910 Laser Light Scattering instrument.

TABLE 6 shows the compositions of formulation I-VI which are used in the ebeam experiments that follow. The polymers used in formulation I-VI are I, Plasdone C-17; II, V, and VI, hydroxyethyl starch 130/0.4; III, Dextran 70; IV, Plasdone C-12; The API is ganaxolone for all formulations except formulation VI. The API is allopregnanolone for formulation VI.

TABLE 6

Composition of formulations I-VI

| Formulation | I | II | III | IV | V | VI* |
|---|---|---|---|---|---|---|
| Ganaxolone | 5.43% | 5.42% | 5.57% | 5.50% | 5.50% | 5.50% |
| Polymer | 5.43% | 5.42% | 5.57% | 5.50% | 11.00% | 5.50% |
| Sodium Deoxycholate | 0.65% | 0.65% | 0.67% | 0.66% | 0.66% | 0.66% |
| Simethicone 30% emulsion | 0.03% | 0.03% | 0.03% | 0.03% | 0.03% | 0.03% |
| Deionized water | 88.46% | 88.46% | 88.16% | 88.31% | 82.81% | 88.31% |
| Total | 100.00% | 100% | 100.00% | 100.00% | 100.00% | 100.00% |

*API was allopregnanolone

TABLE 7 shows the HPLC assay of the neurosteroid and impurity profile for various injectable neurosteroid nanoparticle formulations (I-VI) after ebeam irradiation at 25 KGy (kilo gray). No significant change in impurity profile was observed for any tested formulation.

TABLE 7

| Formulation | Polymer to neurosteroid ratio | HPLC assay (% control) after ebeam @ 25 KGy | Impurity profile after ebeam @ 25 KGy |
|---|---|---|---|
| I | 1 | 100.40 | No change |
| II | 1 | 101.49 | No change |
| III | 1 | 99.22 | No change |
| IV | 1 | 98.01 | No change |
| V | 2 | 99.56 | No change |
| VI | 1 | 99.93 | No change |

TABLE 8 shows the D50 and D90 values for the above injectable neurosteroid nanoparticle formulations (I-VI) before and after ebeam irradiation. Samples contained sucrose at two times the weight percent of neurosteroid.

TABLE 8

| | Unirradiated control | | After ebeam irradition@25 KGy | | | |
| | | | No sucrose | | with Sucrose (2x neurosteroid) | |
| Formulation | D50 (nm) | D90 (nm) | D50 (nm) | D90 (nm) | D50 (nm) | D90 (nm) |
|---|---|---|---|---|---|---|
| I | 168 | 355 | 178 | 415 | 178 | 402 |
| II | 163 | 273 | 171 | 299 | 180 | 383 |
| III | 150 | 231 | 156 | 236 | 163 | 267 |
| IV | 153 | 218 | 155 | 215 | 151 | 215 |
| V | 155 | 238 | 162 | 271 | 170 | 323 |
| VI | 107 | 164 | 107 | 166 | 106 | 164 |

TABLE 9 presents relative viscosity for ganaxolone formulations I-V listed in TABLE 6 before and after ebeam irradiation.

TABLE 9

| Formulation | Relative viscosity before ebeam control | Relative viscosity (after ebeam @ 25 KGy) | % change |
|---|---|---|---|
| I | 2.226 | 2.279 | 2.42% |
| II | 3.178 | 2.850 | −10.32% |
| III | 4.508 | 3.428 | −23.96% |
| IV | 1.853 | 1.856 | 0.16% |
| V | 6.300 | 5.827 | −7.51% |

Example 20. Ebeam Irradiation of Lyophilized Powder of Ganaxolone Nanoparticle Formulations Sucrose (250 mg). was added to the liquid ganaxolone nanoparticle formulation (2 ml) in an 8 ml glass vial and dissolved. The mixture was frozen on dry ice for about 2 hours and lyophilized to obtain a white cake. The compositions of the lyophilized powders are shown in Table 10. The lyophilized powders were subjected to 25 KGy ebeam irradiation. The particle size data were obtained after reconstituting the lyophilized formulations in deionized water.

TABLE 10

Composition, physical and chemical stability of lyophilized ganaxolone nanoparticle powder after ebeam irradiation at a dose of 25 KGy

| Ingredients | Lyophilized powder I (Plasdone C-17) % wt | Lyophilized powder II (Hydroxyethyl starch 130/0.4) % wt | Lyophilized powder III (dextran 70) % wt |
|---|---|---|---|
| Ganaxolone | 22.58% | 22.56% | 22.88% |
| Polymer | 22.58% | 22.56% | 22.88% |
| Na Deoxycholate | 2.70% | 2.71% | 2.75% |
| Simethicone | 0.14% | 0.12% | 0.12% |
| Sucrose | 51.99% | 52.04% | 51.36% |
| Total | 100.00% | 100.00% | 100.00% |
| D50 (nm) | 150 | 188 | 147 |
| D90 (nm) | 266 | 455 | 259 |
| HPLC assay | 97.6% | 97.6% | 95.4% |
| Impurity profile | No change | No change | No Change |

What is claimed is:

1. An injectable neurosteroid formulation comprising stable particle size nanoparticles having a D50 of less than 2000 nm, the nanoparticles comprising
   a) a neurosteroid selected from ganaxolone and allopregnanolone;
   b) hydroxyethyl starch, wherein the (wt:wt) ratio of the neurosteroid to the hydroxyethyl starch is about 4:1 to about 0.5:1; and
   c) an ionic surfactant selected from sodium cholate, sodium deoxycholate, and sodium cholesterol sulfate, and a mixture of any of the foregoing.

2. The injectable neurosteroid formulation of claim 1, comprising nanoparticles having a D50 of less than 500 nm;
   wherein the formulation is an intravenous formulation; and
   the neurosteroid is ganaxolone.

3. The injectable neurosteroid formulation of claim 2, wherein the formulation additionally comprises an antifoaming agent.

4. The injectable neurosteroid formulation of claim 2, wherein the surfactant is sodium deoxycholate.

5. The injectable neurosteroid formulation of claim 2 additionally comprising a cryoprotectant, wherein the cryoprotectant is sucrose, dextrose, lactose, D-sorbitol, or a mixture of any of the foregoing.

6. The injectable neurosteroid formulation of claim 2 additionally comprising one or more of the following
   (a) 0.5% to 1.5% sodium chloride (weight percent);
   (b) a buffer; and
   (c) a preservative, wherein the preservative is benzyl alcohol, chlorbutanol, 2-ethoxyethanol, parabens (including methyl, ethyl, propyl, butyl, and combinations), benzoic acid, sorbic acid, chlorhexidene, phenol, 3-cresol, thimerosal; a phenylmercurate salt, or a mixture of any of the foregoing.

7. The injectable neurosteroid formulation of claim 1, wherein
   the (wt:wt) ratio of the neurosteroid to the hydroxyethyl starch is about 4:1 to about 1:1; and the ionic surfactant is sodium deoxycholate and the ratio of neurosteroid to sodium deoxycholate (w:w) is about 10:1.5 to about 10:0.1.

8. The formulation of claim 7, wherein the formulation is in the form of a lyophilized powder.

9. The formulation of claim 2, wherein the formulation is an aqueous suspension and the neurosteroid concentration is about 0.1 mg/mL to about 300 mg/mL.

10. The injectable neurosteroid formulation of claim 1, wherein the formulation is an aqueous ganaxolone formulation comprising
    (a) nanoparticles having a D50 of less than 500 nm; the nanoparticles comprising ganaxolone, wherein the weight percent of the ganaxolone is 1 to 10%;
    (b) hydroxyethyl starch, wherein the weight percent of the hydroxyethyl starch is 2 to 20%; and
    (c) sodium deoxycholate, wherein the weight percent of the sodium deoxycholate is 0.1% to 2.0%; and
    (d) an antifoaming agent.

11. The injectable neurosteroid formulation of claim 1 wherein the formulation is an aqueous formulation comprising
    (a) nanoparticles having a D50 of less than 500 nm, the nanoparticles comprising ganaxolone, wherein the weight percent of the ganaxolone is about 5%;
    (b) hydroxyethyl starch 130/0.4, wherein the weight percent of the hydroxyethyl starch is about 5% to about 10%;
    (c) sodium deoxycholate, wherein the weight percent of the sodium deoxycholate is about 0.75%; and optionally
    (d) simethicone, wherein the weight percent of simethicone is 0.009%.

12. A method for sterilizing the injectable neurosteroid nanoparticle formulation of claim 2, comprising subjecting the formulation to ebeam radiation, wherein the method produces a sterilized neurosteroid nanoparticle formulation containing a degradant concentration of not more than 0.2% w/w of neurosteroid.

13. The injectable neurosteroid formulation of claim 2, wherein the formulation has been sterilized by ebeam irradiation and wherein the formulation contains a degradant concentration of not more than 0.2% w/w of the neurosteroid.

14. The injectable neurosteroid formulation of claim 13, wherein the ebeam irradiation is a cumulative dose of about 25 kGray.

15. A method of treating a patient having a seizure disorder, stroke, or traumatic brain injury, the method comprising administering intravenously a therapeutically effective amount of the injectable neurosteroid formulation of claim 2.

16. The method of claim 13, wherein the seizure disorder is status epilepticus, refractory status epilepticus, super refractory status epilepticus, or PCDH19 female pediatric epilepsy.

17. The method of claim 15 wherein the dosage of ganaxolone administered is from about 1 mg/kg to about 200 mg/kg.

18. The method of claim 15 comprising administering a single bolus dose of the formulation to the patient; wherein the single bolus dose provides a sufficient amount of ganaxolone to provide a plasma $C_{max}$ of ganaxolone of at least 1000 ng/mL in the patient.

19. The method of claim 15 comprising administering multiple bolus doses of the ganaxolone formulation to the patient, wherein the multiple bolus doses are given over 1 to 10 days at intervals of 1 to 24 hours, wherein each bolus dose provides a sufficient amount of ganaxolone to produce a plasma $C_{max}$ of ganaxolone of at least 1000 ng/mL in the patient.

20. The method of claim 15 comprising administering an intravenous infusion of the ganaxolone formulation to the patient, with or without an initial bolus dose, for 1 to 10 consecutive days at a rate of 1 to 10 mg/kg/hr without an initial bolus dose.

21. The method of claim 20 comprising
administering an initial bolus dose of from about 1 mg/kg to about 20 mg/kg ganaxolone, followed within 24 hours by administration of an intravenous infusion of the ganaxolone formulation for 1 to 10 consecutive days at a rate of 1 to 10 mg/kg/hr; sufficient amount of ganaxolone to provide an initial plasma $C_{max}$ of ganaxolone of at least 1000 ng/mL in the patient and the concentration of ganaxolone in the patient's plasma does not fall below 25% of the initial $C_{max}$ until after the infusion is concluded.

22. The method any one of claim 15 wherein
the injectable ganaxolone formulation is a first active agent and is administered concurrently or sequentially with at least one additional active agent; and
the at least one additional active agent is an anticonvulsant or anesthetic/sedative.

* * * * *